(12) United States Patent
Bennett et al.

(10) Patent No.: US 9,249,425 B2
(45) Date of Patent: Feb. 2, 2016

(54) PROVIRAL PLASMIDS AND PRODUCTION OF RECOMBINANT ADENO-ASSOCIATED VIRUS

(75) Inventors: Jean Bennett, Bryn Mawr, PA (US); Jeannette L. Bennicelli, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/117,312

(22) PCT Filed: May 16, 2012

(86) PCT No.: PCT/US2012/038063
§ 371 (c)(1),
(2), (4) Date: Nov. 12, 2013

(87) PCT Pub. No.: WO2012/158757
PCT Pub. Date: Nov. 22, 2012

(65) Prior Publication Data
US 2014/0087444 A1 Mar. 27, 2014

Related U.S. Application Data

(60) Provisional application No. 61/486,608, filed on May 16, 2011.

(51) Int. Cl.
*C07K 14/435* (2006.01)
*C12N 15/86* (2006.01)
*C12N 15/35* (2006.01)
*C12N 15/864* (2006.01)

(52) U.S. Cl.
CPC ............. *C12N 15/86* (2013.01); *C07K 14/435* (2013.01); *C12N 2750/14111* (2013.01); *C12N 2750/14141* (2013.01); *C12N 2750/14143* (2013.01)

(58) Field of Classification Search
CPC ..... A61K 38/00; A61K 39/23; C07K 14/005; C07K 14/47; C07K 14/015; C12N 15/864; C12N 15/35; C12N 12/12; C12N 15/8645; C12N 2750/14011; C12N 2750/14041; C12N 2750/14043; C12N 2750/14111
See application file for complete search history.

(56) References Cited

U.S. PATENT DOCUMENTS

| | | | |
|---|---|---|---|
| 5,756,283 A * | 5/1998 | Wilson et al. | 435/5 |
| 6,258,595 B1 * | 7/2001 | Gao et al. | 435/320.1 |
| 6,261,551 B1 * | 7/2001 | Wilson et al. | 424/93.2 |
| 8,147,823 B2 | 4/2012 | Acland | |
| 2003/0003582 A1 * | 1/2003 | Wakefield et al. | 435/456 |
| 2004/0219516 A1 * | 11/2004 | Bennett et al. | 435/5 |
| 2007/0077228 A1 * | 4/2007 | Acland et al. | 424/93.2 |
| 2009/0239259 A1 * | 9/2009 | Hsieh | 435/69.1 |
| 2012/0244127 A1 * | 9/2012 | Lipschutz et al. | 424/93.6 |
| 2013/0184332 A1 * | 7/2013 | Linden et al. | 514/44 R |
| 2013/0216500 A1 | 8/2013 | Acland | |

FOREIGN PATENT DOCUMENTS

| | | |
|---|---|---|
| WO | WO 02/078516 | 10/2002 |
| WO | WO 2006/130581 | 12/2006 |

OTHER PUBLICATIONS

Amado DA. "Gene therapy in the retina: Exploring neurotrophic treatment and AAV readministration in retinal disease" (Jan. 1, 2010). Dissertations available from ProQuest. Paper AAI3414128. http://repository.upenn.edu/dissertations/AAI3414128.*
Grieger JC, Samulski RJ. Packaging capacity of adeno-associated virus serotypes: impact of larger genomes on infectivity and postentry steps. J Virol. Aug. 2005;79(15):9933-44.*
Bennicelli J, et. al. Mol Ther. Mar. 2008;16(3):458-65. doi: 10.1038/sj.mt.6300389. Epub Jan. 22, 2008.*
Virus Construction Kit—The Manual. Freiburg_Bioware iGEM 2010. Aug. 4, 2010. http://2010.igem.org/wiki/images/1/12/Manual_-_Virus_Construction_Kit.pdf.*
Balazs, B. et al., Antibody-based protection against HIV infection by vectored immunoprophylaxis, Nature, Jan. 5, 2012, 481(7379): 81-84. Epub: Nov. 30, 2011.
Boulaire, J. et al., Transcriptional targeting to brain cells: Engineering cell type-specific promoter containing cassettes for enhanced transgene expression, Advanced Drug Delivery Reviews, Jul. 2009, 61(7-8): 589-602. Epub: Apr. 23, 2009.
Browne, M. et al., Gene transfer of pigment epithelium-derived factor suppresses tumor growth and angiogenesis in a hepatoblastoma xenograft model, Pediatric Research, Sep. 2006, 60(3): 282-287.

(Continued)

*Primary Examiner* — Benjamin P Blumel
*Assistant Examiner* — Rachel Gill
(74) *Attorney, Agent, or Firm* — Howson & Howson LLP

(57) ABSTRACT

Proviral plasmids contain a modular gene expression cassette with one or a combination of (i) a wildtype 5' AAV2 ITR sequence flanked by unique restriction sites that permit ready removal or replacement of said ITR; (ii) a promoter flanked by unique restriction sites that permit ready removal or replacement of the entire promoter sequence; (iii) a polylinker sequence that permits insertion of a gene coding sequence without modification thereof, wherein the gene is operatively linked to, and under the regulatory control of, the aforementioned promoter; (iv) a bovine growth hormone polyadenylation sequence flanked by unique restriction sites that permit ready removal or replacement of said polyA sequence; and (v) a wildtype 3' AAV2 ITR sequence flanked by unique restriction sites that permit ready removal or replacement of the 3' ITR. These plasmids enable rapid manipulation of the components of the cassette, e.g., rapid mutation and/or replacement of any component, and thereby increase the efficiency of recombinant viral vector, e.g., rAAV, production.

30 Claims, 7 Drawing Sheets

(56) References Cited

OTHER PUBLICATIONS

Chikhlikar, P. et al., Inverted terminal repeat sequences of adeno-associated virus enhance the antibody and CD8<+> responses to a HIV-1 p55Gag/LAMP DNA vaccine chimera, Virology, Jun. 1, 2004, 323(2): 220-232.

Cho, M.A. et al., HoxD10 gene delivery using adenovirus/adeno-associate hybrid virus inhibits the proliferation and tumorigenicity of GH4 pituitary lactotrope tumor cells, Biochemical and Biophysical Research Communications, Jul. 4, 2008, 371(3): 371-374. Epub: Apr. 28, 2008.

Kessler, P.D. et al., Gene delivery to skeletal muscle results in sustained expression and systemic delivery of a therapeutic protein, Proceedings of the National Academy of Sciences, Nov. 26, 1996, 93(24): 14082-14087.

Liu, Y. et al., Specific and efficient transduction of cochlear inner hair cells with recombinant adeno-associated virus type 3 vector, Molecular Therapy, Oct. 2005, 12(4): 725-733. Epub: May 12, 2005.

Song, Y.D. et al., Islet cell differentiation in liver by combinatorial expression of transcription factors Neurogenin-3, BETA2, and RIPE3b1, Biochemical and Biophysical Research Communications, Mar. 9, 2007, 354(2): 334-339. Epub: Jan. 10, 2007.

Yan, Z. et al., Inverted terminal repeat sequences are important for intermolecular recombination and circularization of adeno-associated virus genomes, Journal of Virology, Jan. 2005, 79(1): 364-379.

Auricchio, A. et al., Isolation of highly infectious and pure adeno-associated virus type 2 vectors with a single-step gravity-flow column, Human Gene Therapy, Jan. 1, 2001, 12(1): 71-76.

Bennicelli, J. et al., Reversal of blindness in animal models of leber congenital amaurosis using optimized AAV2-mediated gene transfer, Molecular Therapy, Mar. 19, 2008, 16(3): 458-465. Epub: Jan. 22, 2008.

Hauck, B. et al., Undetectable transcription of *cap* in a clinical AAV vector: Implications for preformed capsid in immune responses, Molecular Therapy, Jan. 2009, 17(1): 144-152. Epub: Oct. 21, 2008.

Maguire, A.M. et al., Safety and efficacy of gene transfer for Leber's congenital amaurosis, New England Journal of Medicine, May 22, 2008, 358: 2240-2248. Epub: Apr. 27, 2008.

Maguire, A.M. et al., Age-dependent effects of RPE65 gene therapy for Leber's congenital amaurosis: a phase 1 dose-escalation trial, Lancet, Jan. 2, 2010, 374(9701): 1597-1605. Epub: Oct. 24, 2009.

Simonelli, F. et al., Gene therapy for Leber's congenital amaurosis is safe and effective through 1.5 years after vector administration, Molecular Therapy, Mar. 2010, 18(3): 643-650. Epub: Dec. 1, 2009.

Wang, C.Y. et al., Astrocytic expression of transgene in the rat brain mediated by baculovirus vectors containing an astrocyte-specific promoter, Gene Therapy, Oct. 2006, 13(20): 1447-1456. Epub: May 25, 2006.

Wang, C.Y. et al., Adeno-associated virus inverted terminal repeats improve neuronal transgene expression mediated by baculoviral vectors in rat brain, Human Gene Therapy, Oct. 2005, 16: 1219-1226. Epub: Sep. 20, 2005.

Flotte, T.R. et al., Adeno-associated virus vectors for gene therapy, Gene Therapy, Aug. 1995, 2(6): 357-362. (Abstract only).

Xu, L. et al., CMV-$\beta$-Actin promoter directs higher expression from an adeno-associated viral vector in the liver than the cytomegalovirus or elongation factor 1$\alpha$ promoter and results in therapeutic levels of human factor X in mice, Human Gene Therapy, Mar. 20, 2001, 12(5): 563-573.

Qu, G. et al., Scaling-up production of recombinant AAV vectors for clinical applications, Current Opinion in Drug Discovery & Development, Nov. 2000, 3(6): 750-755. (Abstract only).

International Search Report dated Sep. 6, 2012 issued in corresponding International Patent Application No. PCT/US/2012/038063.

International Preliminary Report on Patentability dated Nov. 19, 2013 issued in corresponding International Patent Application No. PCT/US2012/038063.

\* cited by examiner

FIG. 7

```
  1 gagaggagccagtcagcagaccggggaccacacgccgcgctgtccccagc 51 acccaacccaggttaccatcggcctccctgttctctggccgcatcctgatc
                       |||||||||||||||||||||||||||||||
  1 ----------------atggcctccctgttctctggccgcatcctgatc 101 cgcaacaatagcgaccaggacgagctggatacggaggctgaggtcagtcg
    |||||||||||||||||||||||||||||||||||||||||||||||||
 34 cgcaacaatagcgaccaggacgagctggatacggaggctgaggtcagtcg 151 caggctggagaaccggctggtgctgctgttctttggtgctggggcttgtc
    |||||||||||||||||||||||||||||||||||||||||||||||||
 84 caggctggagaaccggctggtgctgctgttctttggtgctggggcttgtc 201 cacagtgccaggccttcgtgcccatcctcaaggacttcttcgtgcggctc
    |||||||||||||||||||||||||||||||||||||||||||||||||
134 cacagtgccaggccttcgtgcccatcctcaaggacttcttcgtgcggctc 251 acagatgagttctatgtactgcgggcggctcagctggccctggtgtacgt
    |||||||||||||||||||||||||||||||||||||||||||||||||
184 acagatgagttctatgtactgcgggcggctcagctggccctggtgtacgt 301 gtcccaggactccacggaggagcagcaggacctgttcctcaaggacatgc
    |||||||||||||||||||||||||||||||||||||||||||||||||
234 gtcccaggactccacggaggagcagcaggacctgttcctcaaggacatgc 351 caaagaaatggcttttcctgccctttgaggatgatctgaggaggtgagga
    |||||||||||||||||||||||||||||||||||||||||||||
284 caaagaaatggcttttcctgccctttgaggatgatctgaggagg------

401 ggggcagggagggcttcctggaggaggggcatgttcgctgaaagtgaag 451 catcca
```

US 9,249,425 B2

PROVIRAL PLASMIDS AND PRODUCTION OF RECOMBINANT ADENO-ASSOCIATED VIRUS

CROSS-REFERENCE TO RELATED APPLICATIONS

This application is a national stage of International Patent Application No. PCT/US2012/038063, filed May 16, 2012, which claims the benefit of the priority of U.S. Provisional Patent Application No. 61/486608, filed May 16, 2011 (expired), which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-X5873PCT_ST25.txt"

BACKGROUND OF THE INVENTION

Recombinant adeno-associated virus (rAAV) vectors have been developed for gene replacement therapy because they are non-pathogenic and exhibit a broad range of tissue specificity. These vectors generally retain the AAV inverted terminal repeats (ITRs) located at each end of a gene expression cassette, but lack the AAV rep and cap genes necessary for viral replication and packaging. Therefore rAAV cannot replicate, and viruses must be assembled in packaging cell lines with the rep and cap functions supplied in trans or expressed within the packaging cell itself. The gene expression cassette for insertion into the rAAV conventionally contains the therapeutic gene and the cis-regulatory elements including a promoter and a polyadenylation signal necessary for gene expression. In a conventional method of rAAV production, a gene expression cassette, located between the ITRs, is packaged in rAAV particles, which are then used in therapeutic applications.

The design and construction of the components, such as the plasmids and gene expression cassettes necessary for producing a recombinant AAV, can be quite labor intensive, due to the variety of plasmids and vectors available, and the need to modify the genes to fit into the appropriate plasmids. This complexity is further increased by pharmaceutical industry and governmental requirements that govern the process for obtaining approval of an rAAV for pharmaceutical use.

SUMMARY OF THE INVENTION

The invention described herein involves novel AAV proviral vectors characterized by ease of subcloning and which facilitate the ready substitution of alternative plasmid components. These vectors improve the efficiency of rAAV vector production and function.

In one aspect, a proviral plasmid is provided in which all the functional elements of the proviral plasmids are modular and readily removable or replaceable by virtue of the unique flanking restriction sites. The modular aspect of these plasmids permits the expression of AAVs with different transgenes.

In another aspect, a proviral plasmid comprises a wildtype AAV2 ITR sequence, the ITR flanked by unique restriction sites that permit ready removal from the plasmid or replacement of the entire ITR. In one embodiment, the proviral plasmid comprises a 5' ITR and a 3' ITR as described above, each flanked by different unique restriction sites to permit removal or replacement of each ITR individually.

In another aspect, a proviral plasmid comprises a modular gene expression cassette comprising in operative association, (i) a wildtype 5' AAV2 ITR sequence flanked by unique restriction sites that permit ready removal or replacement of said ITR; (ii) a CMV promoter comprising an upstream non-coding sequence of about 49 nucleotides of CMV to enhance the productivity of the promoter, flanked by unique restriction sites that permit ready removal or replacement of the entire promoter sequence; (iii) a polylinker sequence that permits insertion of a gene coding sequence without modification thereof, wherein the gene is operatively linked to, and under the regulatory control of, the aforementioned promoter; (iv) a bovine growth hormone polyadenylation sequence flanked by unique restriction sites that permit ready removal or replacement of said polyA sequence; and (v) a wildtype 3' AAV2 ITR sequence flanked by unique restriction sites that permit ready removal or replacement of the 3' ITR. In one embodiment, this plasmid contains a cytomegalovirus (CMV) promoter and further comprises an upstream non-coding sequence of about 49 nucleotides of CMV to enhance the productivity of the promoter. In another embodiment, this plasmid contains a hybrid promoter comprising a CMV promoter sequence and a chicken beta actin (CBA) promoter sequence and further comprises an upstream non-coding sequence of about 49 nucleotides of CMV to enhance the productivity of the promoter. In this aspect, the entire promoter is flanked by unique restriction sites that permit ready removal and/or replacement of the enhancer/hybrid promoter sequence.

In another embodiment, the proviral plasmids described above further comprise a plasmid backbone comprising the elements necessary for replication in bacterial cells, and further comprise a kanamycin resistance gene ($Kan^R$), the plasmid backbone containing 5' and 3' transcriptional terminator/insulator sequences that isolate transcription in the backbone from transcription in the gene cassette.

In another embodiment, the proviral plasmids described above further comprise a plasmid backbone comprising the elements necessary for replication in bacterial cells, and further comprise a kanamycin resistance gene ($Kan^R$), the plasmid backbone containing 5' and 3' transcriptional terminator/insulator sequences that isolate transcription in the backbone from transcription in the gene cassette and a lambda stuffer sequence.

In another aspect, a proviral plasmid is p604 of FIG. 1 SEQ ID NO: 1.

In another aspect, a proviral plasmid is p617 of FIG. 2 SEQ ID NO: 2.

In another aspect, a proviral plasmid is p618 of FIG. 3 SEQ ID NO: 3.

In another aspect any of the proviral plasmids described above further comprises a gene encoding sequence inserted into the polylinker sequence.

In another aspect, a method is provided for generating a proviral plasmid as described herein.

In another aspect, a method is provided for generating a rAAV using any of the proviral plasmids described herein.

These and other embodiments and advantages of the invention are described in more detail below.

(i) a synthetic 5' ITR (wildtype AAV 2) (1253-1382) which contains no deletions (1365-1382), the ITR flanked 5' by the unique restriction site SalI (1238) and 3' by the unique restriction site NheI (1428);

(ii) a cytomegalovirus (CMV) promoter (1443-2018) comprising a 49 nucleotide CMV enhancer sequence extension, the CMV enhancer and minimal CMV promoter, the entire promoter flanked 5' by the unique restriction site NheI (1428) and 3' by the unique restriction sites BstXI (2202) and NotI (2208), and the 49 nucleotide enhancer sequence flanked in a 239 nucleotide sequence by 5' NheI (1428) and a 3' unique restriction site NdeI (1667);

(iii) a green fluorescent protein (eGFP) gene (2215-2937) flanked 5' by the unique restriction site BstXI (2202) or NotI (2208) and 3' by the unique restriction sites Hind III (2937), BamHI (2943) and BglII (2952);

(iv) a bovine growth hormone polyadenylation signal (BGH poly A) (2952-3173), flanked 5' by unique restriction sites Hind III (2937), BamHI (2943) and BglII (2952) and 3' by unique restriction site XhoI (3173); and (v) a synthetic 3' ITR (wildtype AAV 2) (3221-3350) which contains no deletions, the ITR flanked 5' by unique restriction site XhoI (3173) and 3' by unique restriction site Bsu36I (3363).

Figure 2:
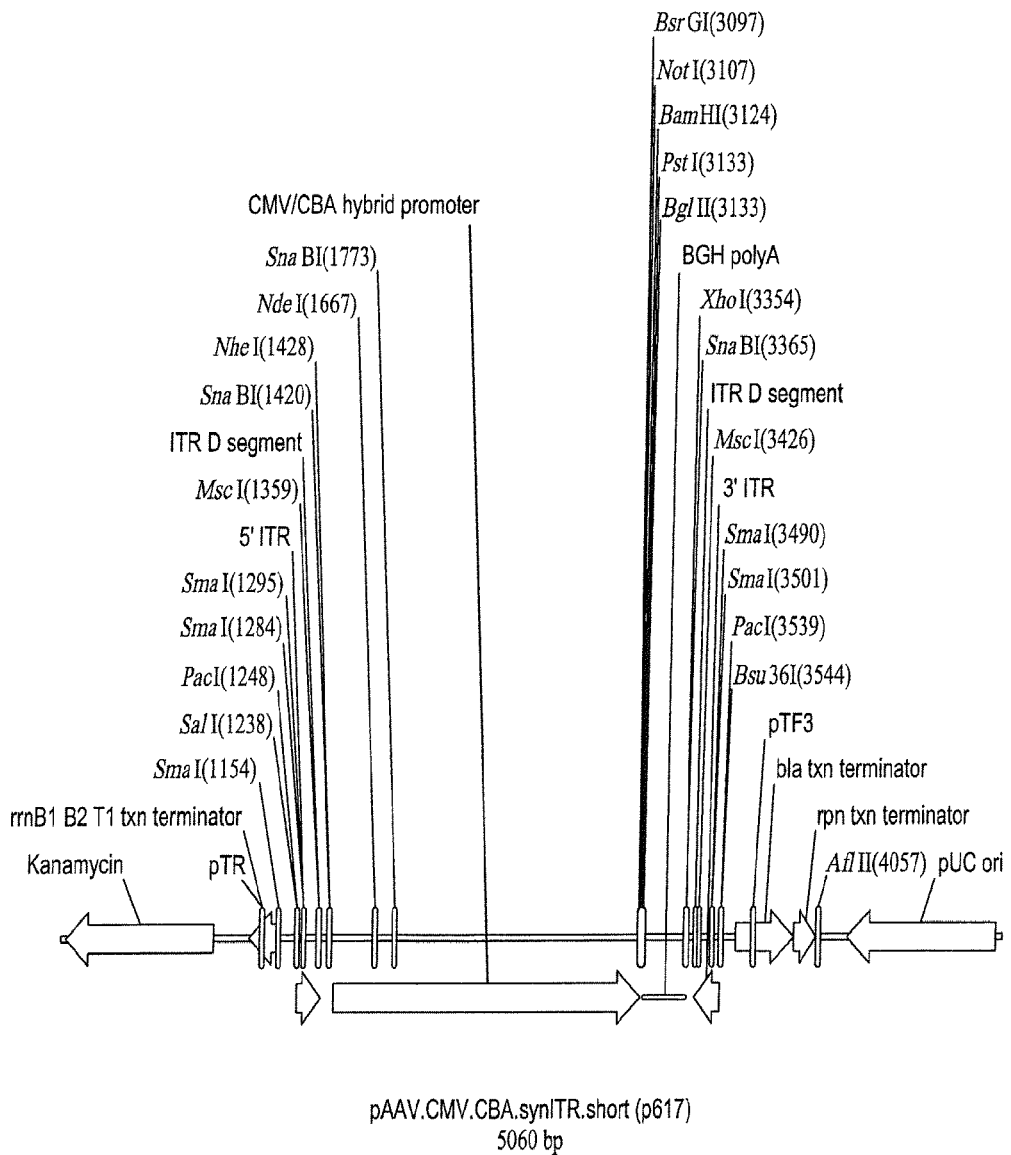

FIG. 2 is a map showing the features of the 5060 bp AAV proviral plasmid pAAV.CMV.CBA.synITR.short (p617). This plasmid contains a modular gene expression cassette in a plasmid backbone based on the pJ201 plasmid (DNA2.0, Menlo Park, Calif.). In the description below, the numbers in parentheses are the nucleotide number in SEQ ID NO: 2. The plasmid backbone contains a kanamycin resistance gene (9-803), pTR (1063-1079), rrn B1 B2 T1 txn terminator sequence (988-1162), a pTF3 (3716-3741), a bla txn terminator (3625-3925), an rpn txn terminator (3932-4045), the restriction site AflII (4057) which may be employed for insertion of a stuffer, and a pUC origin of replication (4217-5020). The gene expression cassette comprises in operative association:

(i) a synthetic 5' ITR (wildtype AAV 2) (1253-1382) which contains no deletions, the ITR flanked 5' by the unique restriction site SalI (1238) and 3' by the unique restriction site NheI (1428);

(ii) a promoter comprising a hybrid CMV/CBA promoter (1443-3104), derived from the pDRIVE CAG plasmid (Invivogen, San Diego, Calif.) with an upstream extension of about 49 nucleotides of CMV enhancer; the entire promoter sequence including the upstream sequence is flanked 5' by the unique restriction site NheI (1428) and 3' by the unique restriction sites NotI (3107), BamHI (3124), PstI (3133) and BglII (3133); the enhancer sequence extension is contained within a 239 nucleotide sequence as described for p604;

(iii) a polylinker sequence containing unique restriction sites NotI (3107), BamHI (3124), PstI (3133) and BglII (3133);

(iv) a bovine growth hormone polyadenylation signal (BGH poly A) (3133-3354), flanked 5' by unique restriction sites NotI (3107), BamHI (3124), PstI (3133) and BglII (3133); and 3' by unique restriction site XhoI (3354);

(v) a synthetic 3' ITR (wildtype AAV 2) (3402-3531) which contains no deletions, the ITR flanked 5' by unique restriction site XhoI (3354) and 3' by unique restriction site Bsu361 (3544).

Figure 3:
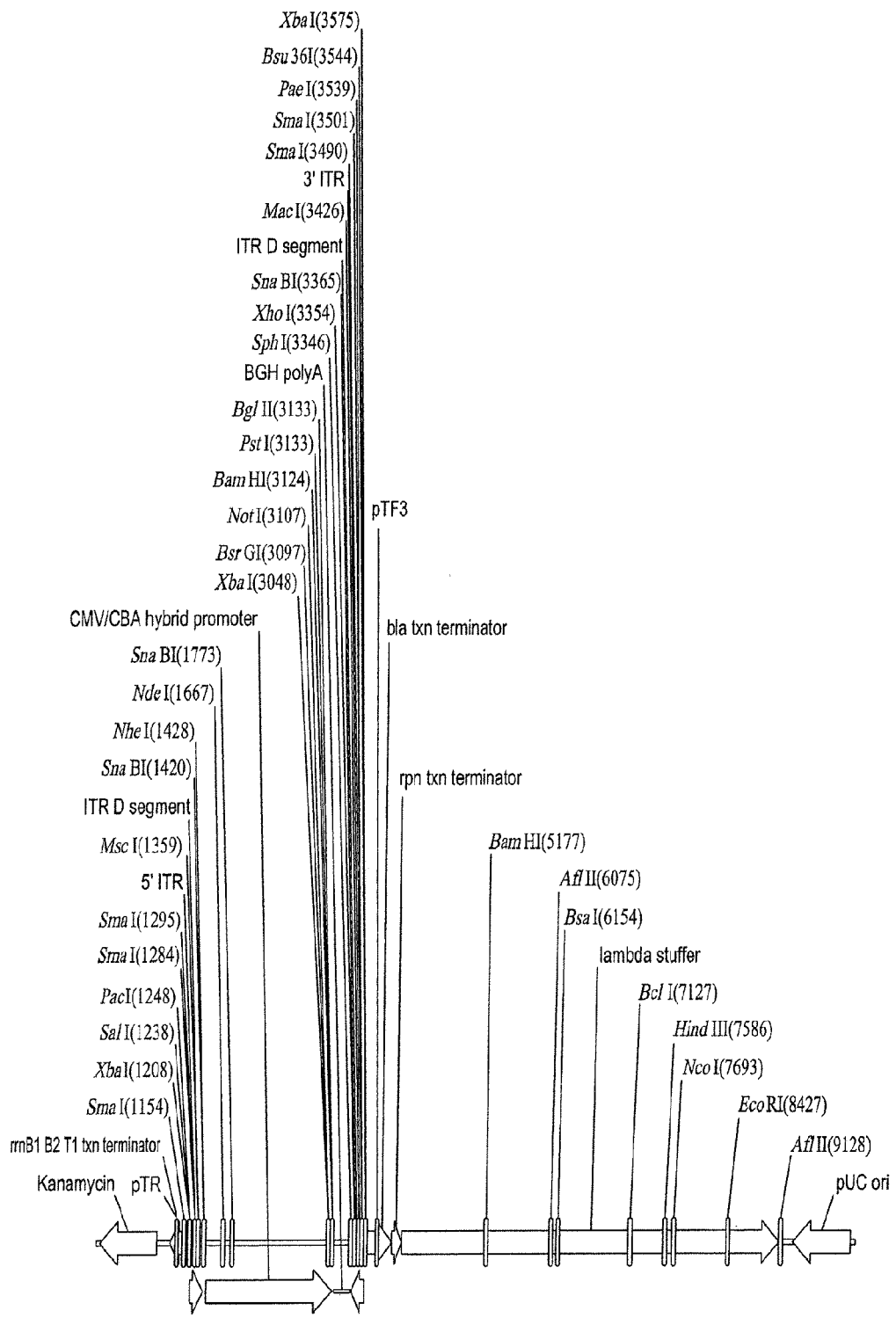

FIG. 3 is a map showing the features of the 10131 bp AAV proviral plasmid pAAV.CMV.CBA.synITRlong.stuffer 15 or p618 (SEQ ID NO: 3). In the description below, the numbers in parentheses are the nucleotide numbers in SEQ ID NO: 3. This plasmid contains a modular gene expression cassette in a plasmid backbone based on the pJ201 plasmid (DNA2.0, Menlo Park, Calif.). The plasmid backbone contains a kanamycin resistance gene (9-803), pTR (1063-1079), rrn B1 B2 T1 txn terminator sequence (988-1162), a pTF3 (3716-3741), a bla txn terminator (3625-3925), an rpn txn terminator (3932-4045), a lambda stuffer sequence (4061-9127) which is inserted into the site AflIII, and a pUC origin of replication (9288-10091).

The gene expression cassette comprises in operative association:

(i) a synthetic 5' ITR (wildtype AAV 2) which contains no deletions, the ITR (1253 to 1382) flanked 5' by the unique restriction site SalI (1238) and 3' by the unique restriction site NheI (1428);

(ii) a promoter comprising a hybrid CMV/CBA promoter, derived from the pDRIVE CAG plasmid (Invivogen, San Diego, Calif.) with an upstream extension of about 49 nucleotides of CMV enhancer, the entire promoter (1443-3104) flanked 5' by the unique restriction site NheI (1428) and 3' by the unique restriction sites NotI (3107), PstI (3133) and BglII (3133); the enhancer sequence extension is contained within a 239 nucleotide sequence as described for p604;

(iii) a polylinker sequence (3105-3137) containing unique restriction sites, NotI (3107), BglII (3133), and PstI (3133);

(iv) a bovine growth hormone polyadenylation signal (BGH poly A) (3133-3354), flanked 5' by unique restriction sites BamHI (2943), BglII (2952), NotI (3107), and PstI (3133) and 3' by unique restriction site XhoI (3354); and (v) a synthetic 3' ITR (wildtype AAV 2) which contains no deletions (3402-3531) flanked 5' by unique restriction site XhoI (3354) and 3' by unique restriction site Bsu36I (3544).

Figure 4:
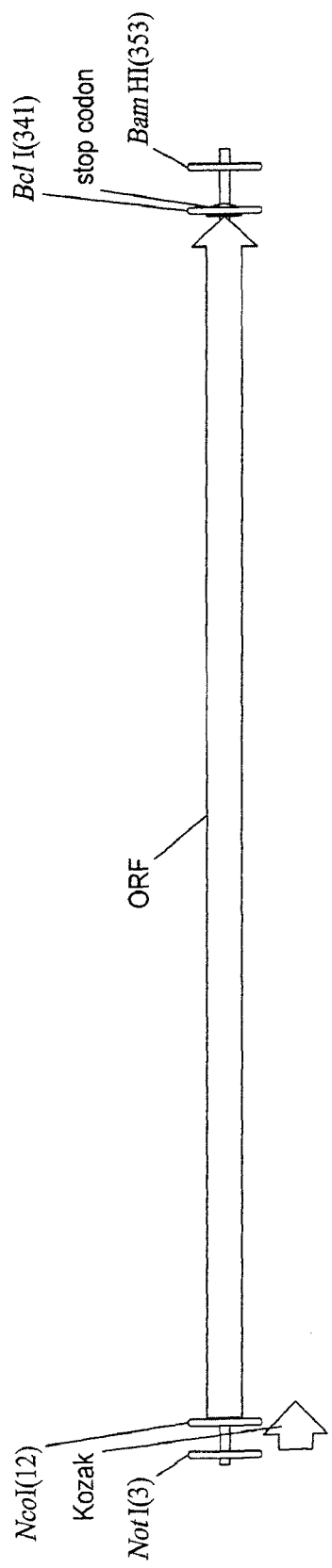

FIG. 4 is a cartoon of the synthesized Exon 1 ORF of hRdCVF1 (DNA2.0) and the modifications made to it for insertion into a proviral plasmid. The modifications include the addition of NotI and BamHI restriction sites, a stop codon embedded in BclI site to facilitate addition of epitope tag, and a complete Kozak consensus sequence that overlaps NotI. Only the hRdCVF1 ORF of SEQ ID NO:4 is included as the transgene. The entire sequence depicts 357 bp.

Figure 5:
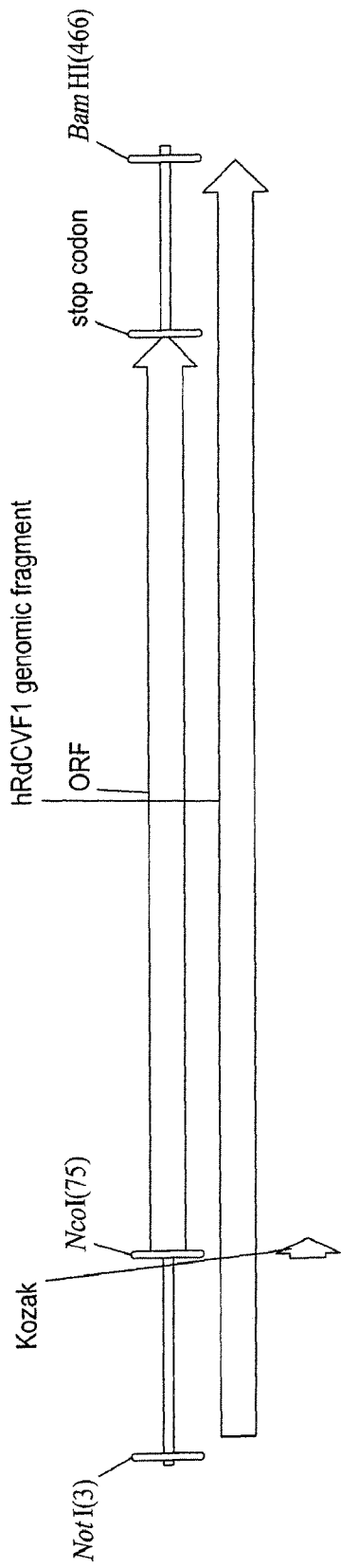

FIG. 5 is a cartoon of a genomic fragment of hRdCVF1 containing the Exon 1 ORF, exonic sequence upstream of the start codon, and intronic sequence downstream of stop codon. Modifications incorporated during synthesis (DNA2.0) include the addition of NotI and BamHI restriction sites. The entire sequence depicts 470 bp.

Figure 6:
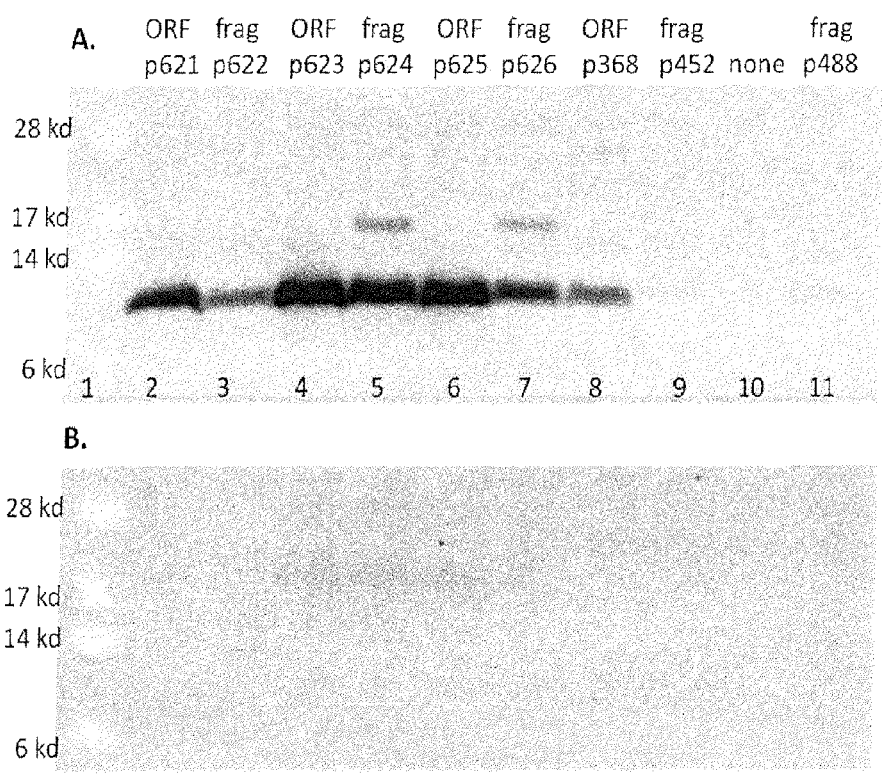

FIG. 6 is a gel showing the results of a Western blot analysis of hRdCVF1 expression in cultured cells after transfection, as described in Example 2.

FIG. 7 is a sequence showing the alignment of hRdCVF1 genomic fragment of 456 bases (top line, SEQ ID NO: 4) and open reading frame or exon 1 ORF of 327 bases (bottom line; SEQ ID NO: 5).

DETAILED DESCRIPTION OF THE INVENTION

The novel AAV proviral plasmids described herein can be used to increase the productivity and efficiency of generating a variety of rAAV expressing a variety of targeted genes. All the functional elements of the proviral plasmids are modular and readily removable or replaceable by virtue of the unique flanking restriction sites. The modular aspect of these plasmids permits the efficient generation of AAVs which express different genes.

I. The Proviral Plasmids

As described herein, a proviral plasmid is designed to include a plasmid "backbone" and a "minigene" or "gene expression cassette" flanked by AAV ITRs. Together the ITRs and minigene comprise the recombinant AAV (rAAV) genome that is packaged into AAV particles.

As discussed in detail herein, the gene expression cassette includes, at a minimum, a transgene (i.e., the gene desired to be transported by the rAAV and expressed in selected cells) and its regulatory sequences, flanked by 5' and 3' AAV inverted terminal repeats (ITRs).

A. Unique Restriction Sites

Every significant component in the rAAV genome contained within the proviral plasmid is flanked by unique restriction sites, i.e., restriction sites used only once in the plasmids to enable ready removal and/or replacement of individual components in the rAAV genome. By "unique restriction site" is meant a restriction site that is cleaved by an enzyme that cannot cleave another restriction site in the proviral plasmid. In one embodiment, the unique flanking restriction enzyme sites allow directional cloning of one or more components into the plasmid. Suitably, a pair of unique restriction enzyme sites flanking one component allows digestion at only a single locus in the proviral plasmid and ready insertion or deletion of only one component of the recombinant AAV genome.

In the present application, suitable restriction enzymes for unique use in the desired plasmids include those identified in the description of the figures and in the figures themselves. Suitable restriction enzymes may be identified using information readily available to those of skill in the art in the literature and in a variety of on-line databases, e.g., the REBASE™ database. Suitable restriction enzymes for the use in generating a proviral plasmid of this invention can be readily determined using a variety of computer programs and/or on-line databases. Suitable restriction enzymes are available from a variety of commercial sources including, e.g., New England Biolabs, Obiogene, Lift Technology, Roche, Clontech, Stratagene, Amersham, Pharmacia, among others.

B. Inverted Terminal Repeats of the Minigene

In one embodiment described herein, a proviral plasmid contains a wildtype ITR of AAV serotype 2. The ITRs are synthesized to remove a common mutation, i.e., a deletion in the upstream ITR that is present in many known vectors. This attribute alone allows use of these plasmids to improve packaging efficiency of rAAV during production. Without wishing to be bound by theory, the inventors theorized that mutated ITR sequences are corrected in the cell during production of the rAAV. However, use of the wildtype ITR, particularly the 5' ITR conserves the cell's resources and is more efficient. However, ITR sequences from other suitable AAV serotype sources may be selected or ITR mutations may be introduced by design to alter function of the rAAV.

In one embodiment, a significant attribute of these plasmids is that the intact wildtype ITR sequence is flanked by unique restriction sites that permit ready removal or replacement of the ITR from the plasmid. Thus, in one embodiment, the proviral plasmid comprises a 5' ITR flanked by unique restriction sites to permit its removal or replacement. In another embodiment, the proviral plasmid comprises a 3' ITR flanked by unique restriction sites to permit its removal or replacement. In another embodiment, the proviral plasmid contains a 5' ITR and a 3' ITR, each ITR flanked by unique restriction sites, so that each ITR may be individually removed from the plasmid, if desired. The proviral plasmids described in the FIGS. 1-3 have identified exemplary ITRs.

This modular capacity of the ITRs in the proviral plasmids allows for ready insertion and replacement of a variety of ITR sequences and permits use of the proviral plasmids in a number of methods for generating recombinant viruses.

C. The Regulatory Sequences of the Minigene

These proviral plasmids also include regulatory elements which are operably linked to the transgene in a manner which permits the transgene's transcription, translation and/or expression in a cell transfected with the plasmid vector or infected with the virus produced generated by use of the proviral plasmids. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

These proviral plasmids are designed so that the promoter and poly A sequences are modular and may be readily replaced with other known promoter and polyA sequences. In one embodiment, e.g., p604 described in detail in FIG. 1, the promoter is a cytomegalovirus promoter (p604) comprising an enhancer and minimal promoter with a 49 nucleotide upstream extension of the enhancer sequence 5'-tagtaatcaat-tacggggtcattagttcatagcccatatatggagttcc-3' (SEQ ID NO: 6). Two unique restriction sites flank a 239 bp promoter fragment that contains this promoter/enhancer extension. Thus, this promoter enhancer/extension, is in fact, modular. One would remove the 239 bp fragment and replace with one without the extension to reduce the power of the promoter.

In another embodiment, the promoter is a hybrid promoter comprising a CMV enhancer sequence and a chicken beta actin (CBA) promoter sequence (the pDRIVE-CAG promoter (Invitrogen). In still another embodiment, the hybrid CMV/CBA promoter further comprises the upstream non-coding sequence of about 49 nucleotides of CMV SEQ ID NO: 6 to enhance the productivity of the promoter, wherein the upstream CMV enhancer/extension sequence is in the larger 239 sequence, discussed above is flanked by unique restriction sites that permit ready removal or replacement of the upstream CMV sequence from the hybrid promoter sequence. In the exemplary plasmids described in detail in FIGS. 1-3, these promoter sequences are identified. It was surprisingly determined that the CMV/CBA hybrid promoter (Invivogen) was about twice as strong a promoter when it is preceded by about a sequence of about 49 nucleotides upstream of the CMV promoter sequence. In the proviral plasmids, this upstream enhancer sequence is flanked by unique restriction sites, permitting its removal and/or replacement should the strong promoter be too strong in expressing any particular transgene in the selected host cell. For example in the three exemplified plasmids, the 49 nucleotide extension SEQ ID NO: 6 is flanked 5' by unique restriction site NheI and further downstream to create the 239 nucleotide sequence by unique restriction site NdeI.

Thus while the identified promoters are currently desirable, the proviral plasmids allow for the easy removal or replacement of the upstream CMV enhancer sequence alone by cleavage at the unique restriction sites flanking the enhancer sequence. In another aspect, the proviral plasmids permit removal or replacement of the entire promoter/enhancer sequence by the presence of unique restriction sites at both ends of the entire promoter sequence.

Should replacement of a promoter sequence be desired these proviral plasmids allow for excision of the existing promoters and insertion between the unique sites of any number of conventionally employed promoters. Suitable constitutive or inducible promoter sequences are available from a variety of commercial sources, including, without limitation, Invitrogen, Clontech and Ariad. Many other systems, e.g., native promoters, tissue-specific promoters, etc., have been described and can be readily selected by one of skill in the art. See, e.g., the promoters identified in U.S. Pat. No. 7,906,111, incorporated by reference herein.

Another modular regulatory sequence in the proviral plasmids described herein is the polyadenylation sequence. In the exemplary plasmids of FIGS. 1-3, the bovine growth hormone polyA site is flanked by unique restriction sites, thereby permitting its ready replacement or removal, as desired. The selection of the particular polyA sequence is not critical. It is a characteristic of these plasmids that quick replacement of this regulatory sequence is possible depending upon the selection of transgene, promoter and/or host cell.

Still other conventional regulatory sequences may be incorporated into the proviral plasmids, as desired.

D. The Poly-Linker Sequence and Transgene of the Minigene

The proviral plasmids described herein also contain a multiple cloning site/polylinker sequence for ready insertion of almost any transgene without the requirement for extensive modification of the transgene. In one embodiment this is due to the inclusion of a number of unique restriction sites, such as NotI, BamHI, PstI and BglII. In FIGS. 2-3 for plasmids p617 and p618, which plasmids have no transgenes, the polylinker sequences are located between the promoter sequence and the polyA sequence. Once a transgene is selected, the transgene (or a portion thereof, if it is a large transgene), may be inserted into the polylinker site of these plasmids.

The transgene is a nucleic acid sequence, heterologous to the ITR and regulatory sequences flanking the transgene, which encodes a polypeptide, protein, RNA, or other product of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. In one embodiment, a reporter sequence is enhanced GFP (eGFP). In p604, for example, the eGFP gene may be easily removed and replaced by any gene up to about 3.3 kb in length for expression in rAAV using current packaging protocols. In other embodiments, such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

However, desirably, the transgene is a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal. Typically, suitable target sequences include oncologic targets and viral diseases. See, for examples of such targets the oncologic targets and viruses identified in U.S. Pat. No. 7,906,111, incorporated herein by reference. In one embodiment, the transgene is the human rod derived cone variability factor 1 (see e.g., NCBI Accession No. NT_011295.11 and NM_138454.1, incorporated by reference; SEQ ID NO: 4). In one embodiment, the transgene is exon 1 open reading frame (ORF) of the hRdCVF1 cDNA, e.g., from the NcoI site at nucleotide 12 to the stop codon and flanked by NotI and BamHI restriction sites (SEQ ID NO: 5; FIG. 4). In another embodiment, the transgene is the exon 1 ORF with exonic sequences upstream of the start codon and intronic sequences downstream of the stop codon flanked by the insertion of a NotI restriction site at nucleotide 3 of the hRdCVf exon 1 fragment and a BamHI restriction site at nucleotide position 466 of the fragment (FIG. 5). In one embodiment, the hRdCVf 1 exon 1 ORF is modified by embedding the stop codon in a MI site at nucleotide position 341 to facilitate the addition of an epitope tag (FIG. 4). A complete Kozak consensus sequence was also included and overlaps the NotI sequence (FIG. 4).

The transgene may be used to correct or ameliorate gene deficiencies, which may include deficiencies in which normal genes are expressed at less than normal levels or deficiencies in which the functional gene product is not expressed. Alternatively, the transgene may provide a product to a cell which is not natively expressed in the cell type or in the host. A preferred type of transgene sequence encodes a therapeutic protein or polypeptide which is expressed in a host cell. The invention further includes using multiple transgenes. In certain situations, a different transgene may be used to encode each subunit of a protein, or to encode different peptides or proteins or portions of a single large protein. This is desirable when the size of the DNA encoding the protein subunit is large, e.g., for an immunoglobulin, the platelet-derived growth factor, or a dystrophin protein. Additionally this may be desirable for proteins encoded by genes that are mutated in inherited forms of blindness such as centrosomal protein 290 kDa (CEP290) mutations in Leber Congenital Amaurosis and ATP-binding cassette, sub-family A member 4 (ABCR).mutations in Stargardt's Disease. In order for the cell to produce the multi-subunit protein, a cell is infected with the recombinant virus containing each of the different subunits. Alternatively, different subunits of a protein may be encoded by the same transgene. In one embodiment, a single transgene includes the DNA encoding each of the subunits, with the DNA for each subunit separated by an internal ribozyme entry site (IRES). This is desirable when the size of the DNA encoding each of the subunits is small, e.g., the total size of the transgene expression cassette including DNA encoding the subunits and the IRES is less than 4.7 kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor. More often, when the transgene is large, consists of multi-subunits, or two transgenes are co-delivered, rAAV carrying the desired transgene(s) or subunits are co-administered to allow them to concatamerize in vivo to form a single vector genome. In such an embodiment, a first AAV may carry an expression cassette which expresses a single transgene and a second AAV may carry an expression cassette which expresses a different transgene for co-expression in the host cell. However, the selected transgene may encode any biologically active product or other product, e.g., a product desirable for study.

Suitable transgenes may be readily selected by one of skill in the art. The selection of the transgene is not considered to be a limitation of this invention, but may be selected from among many known transgenes (see, e.g., transgenes identified in U.S. Pat. No. 7,906,111, incorporated by reference herein). In embodiments, using the proviral plasmids in conventional packaging protocols, plasmid p604 can incorporate transgenes of up to 3.3 kb in length for expression in rAAV; and p617 and p618 can incorporate genes up to 2.4 kb in length.

E. The Backbone of the Proviral Plasmids

In one embodiment, the plasmid backbone of the proviral plasmid includes the conventional elements necessary for replication and, optionally, integration in prokaryotic cells (e.g., bacterial cells). In one embodiment, the plasmid backbone is pJ201 (DNA2.0). See FIGS. 1-3. Still other backbones may be employed if desired expression is mammalian cells, or both.

In one embodiment, the backbone desirably contains a selectable marker, e.g., a kanamycin resistance gene ($Kan^R$). The selectable marker gene is located in the backbone of the proviral plasmid so that it will not be rescued and incorporated into the resulting recombinant virus when the proviral plasmid is used to produce rAAV. It can be used to signal the presence of the plasmids in bacterial cells. $Kan^R$ is particularly useful in these proviral plasmids for the generation of rAAV which are clinically useful or for generation of rAAV used in the treatment of humans for diseases or disorders requiring rAAV-mediated delivery of a particular transgene.

Figure 1:
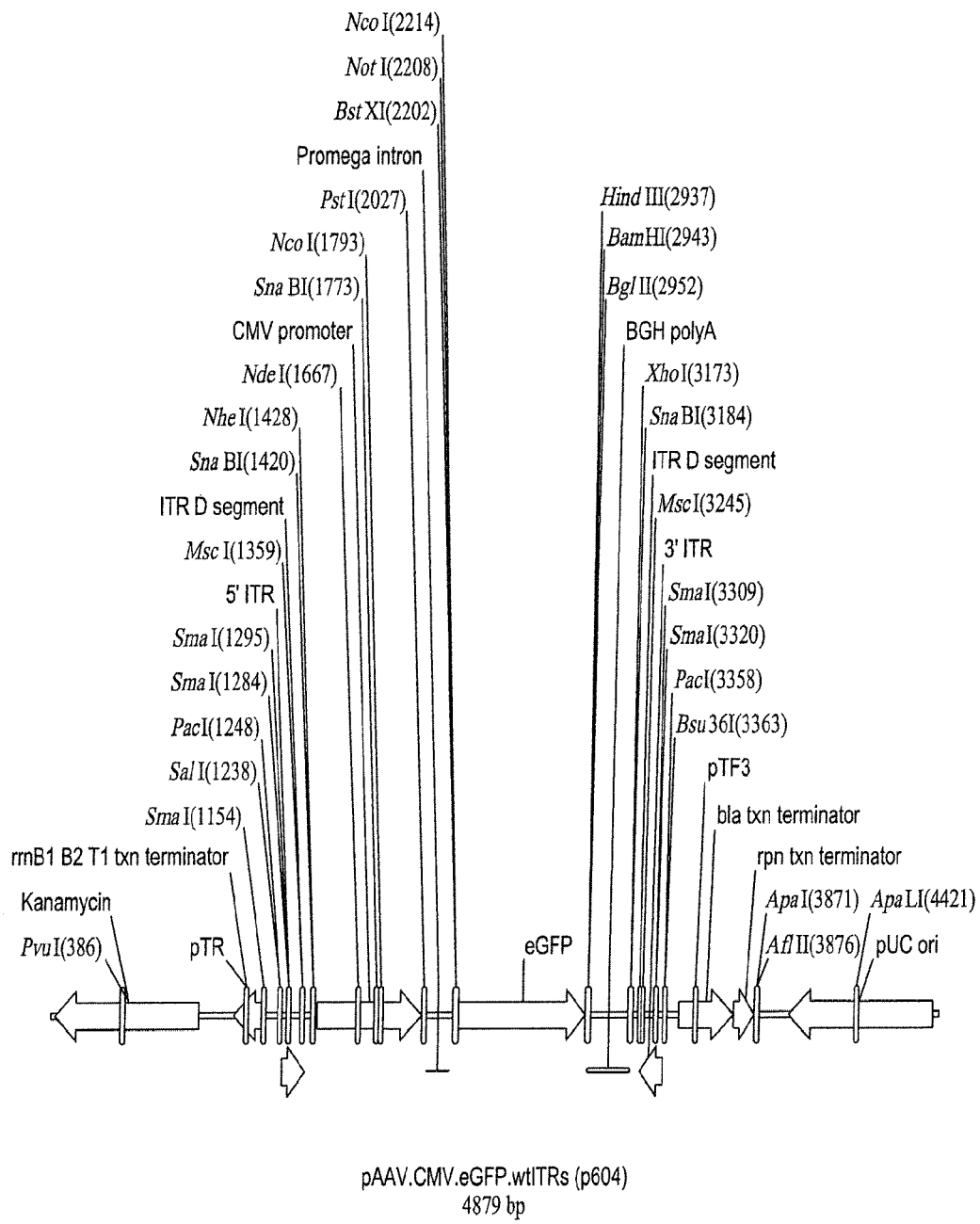
FIG. 1 is a map showing the features of the 4879 bp AAV proviral plasmid pAAV.CMV.eGFP.wtITRs (p604). This plasmid contains a modular gene expression cassette in a plasmid backbone based on the pJ201 plasmid (DNA2.0, Menlo Park, Calif.). In the description below, the numbers in parentheses are the nucleotide number in SEQ ID NO: 1. The plasmid backbone contains a kanamycin resistance gene (9-803), pTR (1063-1079), and nrn B1B2T1 txn terminator sequence (988-1162), a pTF3 (3535-3560), a bla txn terminator (3444-3744), an rpn txn terminator (3751-3864), the restriction site AflII (4057) which may be employed for insertion of a stuffer and a pUC origin of replication (4036-4839). The gene expression cassette comprises in operative association.

In one embodiment, another optional component of the plasmid backbone is an origin of replication, such as the pUC origin of replication identified in FIGS. 1-3.

In another embodiment, the plasmid backbone contains 5' and 3' transcriptional terminator/insulator sequences that isolate transcription in the backbone from transcription in the gene cassette. Among such sequences exemplified in the FIGS. 1-3 are pTR, nrn B1B2T1 txn terminator sequence, pTF3, a bla txn terminator, and an rpn txn terminator.

In another embodiment, the plasmid backbone further comprises a stuffer sequence, such as the stuffer sequence exemplified in p618 (see, FIGS. 2 and 3). A stuffer sequence is a non-coding sequence used to enlarge the backbone. The stuffer sequence contains no functional elements from its viral origin. It does not transcribe genes and contains no promoter. The stuffer, in the case of p618, is a 5.1 kb sequence derived from lambda phage. The stuffer increases the size of the proviral plasmid to greater than 8 kb. It prevents the backbone (i.e., all sequence outside of the recombinant AAV genome) from being packaged into the rAAV capsid, which has a capacity of only 4.7 kb.

Given this description of the proviral plasmids herein, one of skill in the art is expected to be able to select these and other plasmid backbone elements. Many such sequences are available (see, e.g., Sambrook et al, and references cited therein).

The modular proviral plasmids p604, p617 and p618, and variants thereof containing selected transgenes desirably incorporate a variety of the components described herein. p618 in particular is designed as a plasmid that can be used to make a vector for a clinical trial. These features include all of the necessary elements for expression and packaging, except the gene of interest. Any gene can be easily cloned into the multiple cloning site for cDNA that includes NotI, BamHI, PstI, and BglII. The use of these proviral plasmids as described herein improves the ease of subcloning transgenes of a variety of types and sizes into recombinant AAV genomes, facilitates the substitution of alternative plasmid features, and improves the efficiency of rAAV vector production and function. These plasmids may be made by resort to conventional techniques given the descriptions, including sequences provided herein. The method of making the proviral plasmids given this disclosure is within the skill of the art.

II. Generating Recombinant Viruses Using the Proviral Plasmids

The proviral plasmids may be employed in currently conventional packaging methodologies to generate a recombinant virus expressing the transgene carried by the proviral plasmids. Suitable production cell lines are readily selected by one of skill in the art. For example, a suitable host cell can be selected from any biological organism, including prokaryotic (e.g., bacterial) cells, and eukaryotic cells, including, insect cells, yeast cells and mammalian cells. Briefly, the proviral plasmid is transfected into a selected packaging cell, where it may exist transiently. Alternatively, the minigene or gene expression cassette with its flanking ITRs is stably integrated into the genome of the host cell, either chromosomally or as an episome. Suitable transfection techniques are known and may readily be utilized to deliver the recombinant AAV genome to the host cell. Typically, the proviral plasmids are cultured in the host cells which express the cap and/or rep proteins. In the host cells, the gene expression cassettes with flanking AAV ITRs are rescued and packaged into the capsid protein or envelope protein to form an infectious viral particle.

Generally, when delivering the vector comprising the minigene by transfection, the proviral plasmid is delivered in an amount from about 5 µg to about 100 µg DNA, about 10 µg to about 50 µg DNA to about $1\times10^4$ cells to about $1\times10^{13}$ cells, or about $1\times10^5$ cells. However, the relative amounts of plasmid DNA to host cells may be adjusted, taking into consideration such factors as the selected proviral plasmid, the delivery method and the host cells selected.

To avoid undue repetition, reference is made throughout this description to the p618 plasmid. However, it should be appreciated that the other novel plasmids described herein can be constructed and used in a similar manner.

The proviral plasmids described herein, are useful for a variety of purposes, but are particularly well suited for use in production of a recombinant adeno-associated virus containing the gene expression cassette. These plasmids and rAAV vectors, their elements, construction, and uses are known in the art and are described herein.

In one aspect, to generate a recombinant adeno-associated virus (AAV) containing a transgene carried by the p618 plasmid requires the AAV helper functions of the Rep and Cap proteins, and the adenoviral helper functions provided by the products of the adenovirus E2A, E4 and VA genes. In one method, the p618 plasmid is co-transfected into adenovirus-infected human embryonic kidney 293 (293) cells with a plasmid providing the AAV helper functions. In another method, 293 cells are transfected with three plasmids: p618 containing a transgene, a plasmid providing the AAV helper function, and a third plasmid that substitutes for the wild type (wt) adenovirus by providing E2A, E4 and VA adenoviral genes to enable viral replication. The second method offers the advantage of avoiding wt adenovirus infection and of yielding rAAV preparations that are presumed to be free of adenovirus. See, Shi et al, Virology J., 6:3 (January 2009).

The components required to be cultured in the host cell to package a recombinant AAV genome in an AAV capsid may be provided to the host cell in trans. Alternatively, any one or more of the required components (e.g., recombinant AAV genome, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene.

In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein.

The methods used to construct any embodiment of this invention are known to those with skill in nucleic acid manipulation and include genetic engineering, recombinant engineering, and synthetic techniques. Such techniques include conventional cloning techniques of cDNA such as those described in texts (Sambrook et al, Molecular Cloning: A Laboratory Manual, Cold Spring Harbor Press, Cold Spring Harbor, N.Y.), use of overlapping oligonucleotide sequences of the virus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like. See, e.g., K. Fisher et al, *J. Virol.*, 70:520-532 (1993) and U.S. Pat. No. 5,478,745. Similarly, methods of generating rAAV virions are well known and the selection of a suitable method is not a limitation on the present invention.

The AAV and components described herein may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

The host cell contains the sequences which drive expression of a novel AAV capsid protein of the invention (or a capsid protein comprising a fragment thereof) in the host cell and rep sequences of the same source as the source of the AAV ITRs found in the recombinant AAV genome, or a cross-complementing source. The AAV cap and rep sequences may be independently obtained from an AAV source as described above and may be introduced into the host cell in any manner known to one in the art as described above. Additionally, when pseudotyping an AAV vector, the sequences encoding each of the essential rep proteins may be supplied by different AAV sources (e.g., AAV1, AAV2, AAV3, AAV4, AAV5, AAV6, AAV7, AAV8). For example, the rep78/68 sequences may be from AAV2, whereas the rep52/40 sequences may be from AAV8.

In one embodiment, the host cell stably contains the capsid protein under the control of a suitable promoter, such as those described above. Most desirably, in this embodiment, the capsid protein is expressed under the control of an inducible promoter. In another embodiment, the capsid protein is supplied to the host cell in trans. When delivered to the host cell in trans, the capsid protein may be delivered via a plasmid which contains the sequences necessary to direct expression of the selected capsid protein in the host cell. Most desirably, when delivered to the host cell in trans, the plasmid carrying the capsid protein also carries other sequences required for packaging the rAAV, e.g., the rep sequences.

In another embodiment, the host cell stably contains the rep sequences under the control of a suitable promoter, such as those described above. Most desirably, in this embodiment, the essential rep proteins are expressed under the control of an inducible promoter. In another embodiment, the rep proteins are supplied to the host cell in trans. When delivered to the host cell in trans, the rep proteins may be delivered via a plasmid which contains the sequences necessary to direct expression of the selected rep proteins in the host cell. Most desirably, when delivered to the host cell in trans, the plasmid carrying the capsid protein also carries other sequences required for packaging the rAAV, e.g., the rep and cap sequences.

Thus, in one embodiment, the rep and cap sequences may be transfected into the host cell on a single nucleic acid molecule and exist stably in the cell as an episome. In another embodiment, the rep and cap sequences are stably integrated into the chromosome of the cell. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

Optionally, the rep and/or cap sequences may be supplied on a vector that contains other DNA sequences that are to be introduced into the host cells. For instance, the vector may contain the rAAV construct comprising the minigene. The vector may comprise one or more of the genes encoding the helper functions, e.g., the adenoviral proteins E1, Eta, and E4 ORF6, and the gene for VAI RNA.

Preferably, the promoter used in this construct may be any of the constitutive, inducible or native promoters known to one of skill in the art or as discussed above. The selection of the AAV to provide any of these sequences does not limit the invention.

In another preferred embodiment, the promoter for rep is an inducible promoter, such as are discussed above in connection with the transgene regulatory elements. One preferred promoter for rep expression is the T7 promoter. The vector comprising the rep gene regulated by the T7 promoter and the cap gene, is transfected or transformed into a cell which either constitutively or inducibly expresses the T7 polymerase. See International Patent Publication No. WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or a coding sequence with transcriptional controls. Two exemplary sources of spacer sequences are the phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Although the molecule(s) providing rep and cap may exist in the host cell transiently (i.e., through transfection), it is preferred that one or both of the rep and cap proteins and the promoter(s) controlling their expression be stably expressed in the host cell, e.g., as an episome or by integration into the chromosome of the host cell. The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep or cap protein may be provided stably by a host cell.

The packaging host cell also requires helper functions in order to package the rAAV of the invention. Optionally, these functions may be supplied by a herpesvirus. Most desirably, the necessary helper functions are each provided from a human or non-human primate adenovirus source, such as those described above and/or are available from a variety of sources, including the American Type Culture Collection (ATCC), Manassas, Va. (US). In one currently preferred embodiment, the host cell is provided with and/or contains an E1a gene product, an E1b gene product, an E2a gene product, and/or an E4 ORF6 gene product. The host cell may contain other adenoviral genes such as VAI RNA, but these genes are not required. In a preferred embodiment, no other adenovirus genes or gene functions are present in the host cell.

By "adenoviral DNA which expresses the E1a gene product", it is meant any adenovirus sequence encoding E1a or any functional E1a portion. Adenoviral DNA which expresses the E2a gene product and adenoviral DNA which expresses the E4 ORF6 gene products are defined similarly. Also included are any alleles or other modifications of the adenoviral gene or functional portion thereof. Such modifications may be deliberately introduced by resort to conventional genetic engineering or mutagenic techniques to enhance the adenoviral function in some manner, as well as naturally occurring allelic variants thereof. Such modifications and methods for manipulating DNA to achieve these adenovirus gene functions are known to those of skill in the art.

The adenovirus E1a, E1b, E2a, and/or E4ORF6 gene products, as well as any other desired helper functions, can be provided using any means that allows their expression in a cell. Each of the sequences encoding these products may be on a separate vector, or one or more genes may be on the same vector. The vector may be any vector known in the art or disclosed above, including plasmids, cosmids and viruses. Introduction into the host cell of the vector may be achieved by any means known in the art or as disclosed above, including transfection, infection, electroporation, liposome delivery, membrane fusion techniques, high velocity DNA-coated pellets, viral infection and protoplast fusion, among others. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously added factors, for example.

The host cell itself may be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it not carry any adenovirus gene other than E1, E2a and/or E4 ORF6; it not contain any other virus gene which could result in homologous recombination of a contaminating virus during the production of rAAV; and it is capable of infection or transfection of DNA and expression of the transfected DNA. In a preferred embodiment, the host cell is one that has rep and cap stably transfected in the cell.

One host cell useful in the present invention is a host cell stably transformed with the sequences encoding rep and cap, and which is transfected with the adenovirus E1, E2a, and E4ORF6 DNA and a proviral plasmid carrying the recombinant AAV genome as described above. Stable rep and/or cap expressing cell lines, such as B-50 (International Patent Application Publication No. WO 99/15685), or those described in U.S. Pat. No. 5,658,785, may also be similarly employed. Another desirable host cell contains the minimum adenoviral DNA which is sufficient to express E4 ORF6. Yet other cell lines can be constructed using the novel AAV9 cap sequences of the invention.

The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods which provide the desired nucleotide sequence.

Introduction of the proviral plasmids discussed herein and the other necessary elements into the host cell may also be accomplished using techniques known to the skilled artisan and as discussed throughout the specification. See, also, S. Shi et al, Virol. J., 6:3 (2009). In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins).

The resulting recombinant AAV that express the product of the transgene is particularly well suited to gene delivery for therapeutic purposes and for immunization, including inducing protective immunity. Further, the compositions of the invention may also be used for production of a desired gene product in vitro. For in vitro production, a desired product (e.g., a protein) may be obtained from a desired culture following transduction of host cells with a rAAV containing the molecule encoding the desired product and culturing the cell culture under conditions which permit expression. Alternatively a desired product may be obtained from a desired culture following transfection of host cells with proviral plasmid containing the desired transgene. The expressed product may then be purified and isolated, as desired. Suitable techniques for transfection, cell culturing, purification, and isolation are known to those of skill in the art.

The following examples are illustrative only, and do not limit the scope of the present invention.

EXAMPLE 1

Construction of AAV Proviral Plasmids Containing Human RdCVF1

NCBI reference NT_011295.11, *Homo sapiens* chromosome 19 genomic contig, GRCh37.p2 reference primary assembly contains the nucleotedoxin-like protein 1 or rod-derived cone viability factor 1 (RdCVF1). The mRNA reference sequence is NM_138454.1 (SEQ ID NO: 4).

A fragment including exon 1 with 5' UTR as well as upstream and downstream flanking intronic sequence, with a stop codon in the downstream intron is used. Exon 1 begins at nt 21 of the genomic fragment.

Based on the reference sequences, two DNA fragments comprising the open reading frame (ORF) and a genomic fragment are synthesized by DNA2.0. The latter is synthesized as a 470 bp fragment with 5' NotI and 3' BamHI sites to facilitate cloning. The 357 bp ORF cDNA is synthesized with a complete Kozak consensus sequence that was partly embedded in a 5' NotI site. The stop codon is embedded in a BclI site, followed by a BamHI site. The BclI site is inserted to allow addition of epitope tags. Each fragment was synthesized by DNA2.0 and supplied in a plasmid vector pJ201.

Each fragment (ORF and genomic fragment, SEQ ID NOs: 5 and 4, respectively) is subcloned into AAV proviral plasmids pAAV.CMV.CBA.synITR.short (p617), and pAAV.CMV.CBA.synITR.long (p618) and into an additional known plasmid. The resulting plasmids p623/ORF and p624/genomic fragment were derived from p617. The resulting plasmids p625/ORF and p626/genomic fragment are derived from plasmid p618.

EXAMPLE 2

Western Blot Assay

Plasmids included the newly made AAV-hRdCVF1 proviral plasmids described in Example 1, as well as pAAV2.1 CMV.hRdCVF1 (p368), another plasmid made by the inventors, and two pcDNA3-based plasmids p452 and p488 supplied by a third party.

To determine expression levels of RdCVF1 from the plasmids, a Western blot experiment was performed as follows: 293T cells (passage number n+5) were seeded into 100 mm culture dishes. At 24 hours after seeding, the cells were approximately 30% confluent and were transfected with 25 µg/dish of endotoxin-free plasmid (Quiagen) using lipofectamine LTX (ratio 2.5 µl lipofectamine LTX per µg of plasmid).

The cell culture medium was DMEM with high glucose, no pyruvate, and 10% FBS (no antibiotic). At 6 h the medium was aspirated and replaced with 5 ml of serum-free Optimem medium per dish. 24 h post transfection, the conditioned media were collected and spun for 5 min at 1200 rpm to remove cells and debris. A protease inhibitor cocktail was added to the clarified media and they were stored at −80° C. until use. Cells were scraped from each dish into PBS, and the collected cells were pooled with the cells collected from the conditioned medium. Each cell pellet was resuspended in 250 µl of RIPA containing protease inhibitor cocktail. After 1 h incubation on ice, DNA was cleared from each sample by passage of the lysate over glass beads. A Pierce Micro BCA kit was used to quantify protein, and 50 µg aliquots of cell lysate were made and frozen at −80° C.

On the day of the assay, conditioned media were thawed and concentrated at 4° C. using Amicon Ultra-15 concentrators with a 3 Kd cut-off. 5 ml of conditioned medium was concentrated to 400 µl volume (12.5×). Samples consisted of 50 µg cell lysate (in a volume of 21 µl) or 21 µl of concentrated, conditioned medium. Each sample represented roughly $\frac{1}{20}^{th}$ of the entire contents of the culture dish. Samples were denatured in 1×LDS loading buffer (Invitrogen) with DTT for 10 min at 70° C. and loaded onto NuPAGE 4-12% gradient Bis-Tris gels that were subsequently run in MES buffer (Invitrogen). Gels were electroblotted onto Hybond ECL nitrocellulose (Amersham) and the transfer was verified by Ponceau staining.

Blots were blocked ON at 4° C. using 5% milk in PBS with 0.05% Tween-20, followed by ON incubation at 4° C. in primary antibody (p51181 J67) diluted 1:5000 in 3% milk in PBS-Tween-20. Incubation with the secondary antibody was 3 h at RT using a 1:15,000 dilution of donkey anti-rabbit Ig-HRP conjugated (Amersham ECL reagent). The HRP signal was detected using ECL-Plus reagent and a Typhoon scanner. Results are shown in FIG. 6.

As shown (FIG. 6A), all of the newly synthesized AAV proviral plasmids (lanes 2-7) as well as the inventors' additional plasmid (lane 8) express a strong band, between the 6 and 14 kd molecular weight markers that is detected by antibody p51181 J67 and is consistent with the predicted size of 12.7 kd for hRdCVF1. The two pcDNA3-based plasmids provided by a third party (lanes 9 and 11) express a faint band that is slightly larger than the bands expressed by the other plasmids. Finally, plasmids p624 (lane 5) and p626 (lane 7) express a band just below the 17 kd molecular weight marker that most likely represents a product resulting from an incomplete translational stop at the predicted stop codon immediately after the ORF. Finally, plasmids p623, p624 (based on p617), p625 and p626 (based on p618) show increased expression of the 12.7 kd band relative to p621 and p622, indicating that the addition of upstream CMV sequences in the plasmids results in a more powerful promoter. In fact, the postulated read-through at the stop codon in plasmids containing the hRdCVF1 genomic fragment is not seen in plasmid p622 (lane 3) which has a less powerful promoter than p624 (lane 5) and p626 (lane 7). Finally, there is no evidence of secretion of hRdCVF1 in this experiment (FIG. 6B).

The best prospects for in vivo use are p625 and p626. The former is best for robust expression of a product of uniform length. The latter would be useful if the longer product is biologically relevant. These two p618-based plasmids are preferred over p623 and p624 that perform similarly, but do not contain a stuffer in the plasmid backbone. These plasmids do not contain a deletion in the upstream ITR, and as judged by band intensities in the Western blots, the promoter appears to be twice as strong as the promoter in p621 and p622 which lacks the 49 nucleotide-long extension of the CMV enhancer.

EXAMPLE 3

Production of rAAV

As discussed in Example 2 above, human Rod-derived Cone Variability Factor 1 is introduced into p618 under control of the 49 nucleotide CMV enhancer/CMV-CBA hybrid promoter by insertion into the polylinker following digestion of p618 with the unique restriction enzymes NotI and BamHI. Following this transgene insertion, the proviral plasmid was called p625.

Proviral plasmid p625 is co-transfected into a stable rep and cap expressing host packaging cell line B-50 (International Patent Application Publication No. WO 99/15685) with the adenovirus E1, E2a, and E4ORF6 DNA. The gene expression cassette from the proviral plasmid is packaged into AAV particles employing iodixanol gradient purification followed by herparin-sepharose agarose column chromatography. Vector titers are determined using an infectious center assay. AAV-hRdCVF1 virus preparations are made and combined to a desired total volume.

The rAAV-hRdCVF1 may be employed, for example, to transduce cultured target cells in vitro at multiplicities of infection (MOI) ranging from $10^3$ to $10^6$ rAAV viral particles per cell. Additionally, rAAV-hRdCVF1 may be employed in vivo to transduce cells of the murine or other mammalian retina after administration by subretinal injection of $10^{11}$-$10^{13}$ viral particles. Expression of hRdCVF1 in transduced cells or retinas is assessed by RT-PCR, immunocytochemistry, immunohistochemistry, and Western blot analysis, using conventional techniques.

All publications and documents recited above, the Sequence Listing, and the entirety of U.S. Provisional Patent Application No. 61/486,608, filed May 16, 2011, are incorporated herein by reference. Numerous modifications and variations are included in the scope of the above-identified specification and are expected to be obvious to one of skill in the art. Such modifications and alterations to the compositions and processes, such as selections of different AAV species and subtypes, are believed to be within the scope of the claims appended hereto.

TABLE 1

(Sequence Listing Free Text)
The following information is provided for sequences containing free text under numeric identifier <223>.

| SEQ ID NO: (containing free text) | Free text under <223> |
| --- | --- |
| 1 | Synthetic Construct |
| 2 | Synthetic Construct |
| 3 | Synthetic Construct |
| 4 | Homo sapiens |
| 5 | Homo sapiens |
| 6 | Cytomegalovirus |

The invention claimed is:

1. A proviral plasmid comprising a modular recombinant AAV genome comprising:
   (a) a 5' AAV ITR sequence, the ITR flanked upstream by restriction site 1 and downstream by restriction site 2;
   (b) a promoter flanked upstream by restriction site 2 and downstream by restriction site 3; wherein the promoter is a hybrid promoter comprising the cytomegalovirus (CMV) promoter/chicken beta actin (CBA) promoter (CMV/CBA promoter), and wherein the hybrid promoter further comprises an upstream non-coding CMV enhancer sequence of SEQ ID NO:6;
   (c) a polylinker sequence comprising restriction site 3, restriction site 4 and restriction site 5, that permits insertion of a heterologous nucleic acid sequence between any two of the restriction sites 3, 4 and 5, without modification thereof, wherein the heterologous sequence is operatively linked to, and under the regulatory control of, said promoter;
   (d) a polyadenylation sequence flanked upstream by restriction site 4 or 5 and downstream by restriction site 6; and
   (e) a 3' AAV ITR sequence flanked upstream by restriction site 6 and downstream by restriction site 7;
   wherein each said restriction site 1 through 7 occurs only once in the plasmid and is cleaved by a different enzyme that cannot cleave another restriction site in the plasmid, and wherein said restriction sites 1 through 7 are positioned to permit independent removal, replacement or substitution of one or more of element (a), (b), (c), (d) and (e) or the entire AAV genome (a) through (e) from the plasmid.

2. The plasmid according to claim 1, wherein the 5'AAV ITR is a 5' AAV2 ITR sequence.

3. The plasmid according to claim 1, further comprising a plasmid backbone comprising elements necessary for replication in bacterial cells, and a resistance gene.

4. The plasmid according to claim 3, wherein the plasmid backbone further comprises one or more of (a) 5' and 3' transcriptional terminator/insulator sequences that isolate transcription in the backbone from transcription in the modular recombinant AAV genome; or (b) a non-coding stuffer sequence that increases the backbone length and prevents reverse packaging of non-functional AAV genomes.

5. The proviral plasmid according to claim 1, further comprising a plasmid backbone comprising elements necessary for replication in bacterial cells, and a kanamycin resistance gene, said plasmid backbone flanked by transcriptional terminator/insulator sequences that isolate transcription in the backbone from transcription in the modular recombinant AAV genome.

6. The plasmid according to claim 4, wherein said non-coding stuffer sequence is a lambda phage 5.1 kb stuffer sequence.

7. The plasmid according to claim 1, further comprising within the polylinker a heterologous nucleotide sequence.

8. The plasmid according to claim 1, further comprising within the polylinker a heterologous nucleotide sequence encoding human rod derived cone viability factor exon 1 or a fragment thereof.

9. The plasmid according to claim 1, further comprising within the polylinker a heterologous nucleotide sequence which encodes a detectable reporter.

10. An in vitro cell culture comprising cells transfected with the plasmid according to claim 7.

11. The proviral plasmid according to claim 1, wherein the restriction site 1 is SalI; restriction site 2 is NheI; restriction site 3 is NotI; restriction site 4 is PstI; restriction site 5 is BglII; restriction site 6 is Sph I or Xho I; and restriction site 7 is Bsu36I.

12. The plasmid according to claim 1, wherein the polylinker sequence further comprises one or more additional restriction sites that permits insertion of a gene coding sequence between said additional restriction sites, or between restriction site 4 and additional restriction site, between restriction site 5 and additional restriction site, between restriction site 6 and additional restriction site without modification of the restriction sites, wherein the gene is operatively linked to, and under the regulatory control of, said promoter;
wherein each additional restriction site occurs only once in the plasmid and is cleaved by a different enzyme that cannot cleave another restriction site in the plasmid, thereby permitting removal or replacement of said gene coding sequence from the polylinker sequence of the plasmid.

13. The plasmid according to claim 12, wherein said additional restriction sites are restriction sites BxtXI, HindIII and BamHI.

14. The plasmid according to claim 1, further comprising an additional restriction site positioned between the polyadenylation sequence and the 3' AAV ITR, wherein said additional restriction site occurs only once in the plasmid and is cleaved by a different enzyme that cannot cleave another restriction site in the plasmid.

15. A proviral plasmid comprising a modular recombinant AAV genome comprising:
(a) a 5' AAV2 ITR sequence, the ITR flanked upstream by restriction site 1 and downstream by restriction site 2;
(b) a hybrid promoter comprising SEQ ID NO:6 upstream of a CMV/CBA promoter sequence, wherein the hybrid promoter is flanked upstream by restriction site 2 and downstream by restriction site 3 that permit ready removal or replacement of the entire promoter sequence, and wherein SEQ ID NO:6 is flanked by restriction site 2 and restriction site 8, wherein said restriction sites 2 and 8 permit ready removal or replacement of SEQ ID NO:6 separately from the CMV/CBA promoter sequence;
(c) a polylinker sequence comprising restriction sites 3, 4 and 5 that permit insertion of a heterologous nucleotide sequence between any two of restriction sites 3, 4 and 5, wherein the heterologous nucleotide sequence is operatively linked to, and under the regulatory control of, said promoter;
(d) a bovine growth hormone polyadenylation sequence flanked upstream by restriction site 5 and downstream by restriction site 6; and
(e) a 3' AAV2 ITR sequence flanked upstream by restriction site 6 and downstream by restriction site 7;
said plasmid further comprising a plasmid backbone comprising elements necessary for replication in bacterial cells, a resistance gene, said plasmid backbone flanked by transcriptional terminator/insulator sequences that isolate transcription in the backbone from transcription in the modular recombinant AAV genome;
wherein each said restriction sites 1 through 8 occurs only once in the plasmid and is cleaved by a different enzyme that cannot cleave another restriction site in the plasmid, thereby permitting independent removal or replacement or substitution of one or more of element (a), (b), (c), (d) and (e) or the entire AAV genome from (a) through (e) from the plasmid; and permitting independent removal or replacement of the upstream CMV enhancer sequence of SEQ ID NO:6 separately from the CMV/CBA promoter sequence in the plasmid.

16. The plasmid according to claim 15, further comprising within the polylinker a heterologous nucleotide sequence.

17. The plasmid according to claim 15, further comprising within the polylinker a heterologous nucleotide sequence encoding human rod derived cone viability factor exon 1 or a fragment thereof.

18. The plasmid according to claim 15, wherein the polylinker sequence further comprises one or more additional restriction sites that permits insertion of a gene coding sequence between said additional restriction sites, or between restriction site 4 and additional restriction site, between restriction site 5 and additional restriction site, between restriction site 6 and additional restriction site without modification of the restriction sites, wherein the gene is operatively linked to, and under the regulatory control of, said promoter;
wherein each additional restriction site occurs only once in the plasmid and is cleaved by a different enzyme that cannot cleave another restriction site in the plasmid, thereby permitting removal or replacement of said gene coding sequence from the polylinker sequence of the plasmid.

19. The plasmid according to claim 18, wherein said additional restriction sites are one or more of restriction sites BxtXI, HindIII and BamHI.

20. A proviral plasmid comprising a modular recombinant AAV genome, wherein the plasmid comprises a polylinker within said genome, and wherein the plasmid comprises the nucleotide sequence of SEQ ID NO: 3.

21. The plasmid according to claim 20, further comprising within the polylinker a heterologous nucleotide sequence.

22. The plasmid according to claim 20, further comprising within the polylinker a nucleotide sequence encoding human rod derived cone viability factor exon 1 or a fragment thereof.

23. An in vitro cell culture comprising cells transfected with the plasmid according to claim 21.

24. A proviral plasmid comprising a modular recombinant AAV genome, wherein the plasmid comprises a polylinker within said genome, wherein the plasmid comprises the nucleotide sequence of SEQ ID NO: 2.

25. The plasmid according to claim 24, further comprising within the polylinker a heterologous nucleotide sequence.

26. The plasmid according to claim 24, further comprising within the polylinker a heterologous nucleotide sequence encoding human rod derived cone viability factor exon 1 or a fragment thereof.

27. A proviral plasmid comprising a modulator recombinant AAV genome, wherein the plasmid comprises a polylinker within said genome and a heterologous nucleotide sequence encoding green fluorescent protein (GFP) within the polylinker, and wherein the plasmid comprises the nucleotide sequence of SEQ ID NO: 1.

28. A proviral plasmid produced by replacing the heterologous nucleotide sequence encoding GFP in the polylinker of the plasmid of claim 27 with another heterologous nucleotide sequence.

29. The plasmid according to claim 1, wherein the polyadenylation sequence is a bovine growth hormone polyadenylation sequence.

30. The plasmid according to claim 1, wherein the 3' AAV ITR is a 3' AAV2 ITR sequence.

* * * * *

SEQUENCE LISTING

<160> NUMBER OF SEQ ID NOS: 6

<210> SEQ ID NO 1
<211> LENGTH: 4879
<212> TYPE: DNA
<213> ORGANISM: Artificial Sequence
<220> FEATURE:
<223> OTHER INFORMATION: proviral plasmid p604 from adeno-associated
      virus

<400> SEQUENCE: 1
tagaaaaact catcgagcat caaatgaaac tgcaatttat tcatatcagg attatcaata    60

```
ccatatttt  gaaaaagccg  tttctgtaat  gaaggagaaa  actcaccgag  gcagttccat   120
aggatggcaa  gatcctggta  tcggtctgcg  attccgactc  gtccaacatc  aatacaacct   180
attaatttcc  cctcgtcaaa  ataaggttta  tcaagtgaga  atcaccatg   agtgacgact   240
gaatccggtg  agaatggcaa  aagtttatgc  atttctttcc  agacttgttc  aacaggccag   300
ccattacgct  cgtcatcaaa  atcactcgca  tcaaccaaac  cgttattcat  tcgtgattgc   360
gcctgagcga  ggcgaaatac  gcgatcgctg  ttaaaaggac  aattacaaac  aggaatcgag   420
tgcaaccggc  gcaggaacac  tgccagcgca  tcaacaatat  tttcacctga  atcaggatat   480
tcttctaata  cctggaacgc  tgttttccg   gggatcgcag  tggtgagtaa  ccatgcatca   540
tcaggagtac  ggataaaatg  cttgatggtc  ggaagtggca  taaattccgt  cagccagttt   600
agtctgacca  tctcatctgt  aacatcattg  caacgctac   ctttgccatg  tttcagaaac   660
aactctggcg  catcgggctt  cccatacaag  cgatagattg  tcgcacctga  ttgcccgaca   720
ttatcgcgag  cccatttata  cccatataaa  tcagcatcca  tgttggaatt  taatcgcggc   780
ctcgacgttt  cccgttgaat  atggctcata  ttcttccttt  ttcaatatta  ttgaagcatt   840
tatcagggtt  attgtctcat  gagcggatac  atatttgaat  gtatttagaa  aaataaacaa   900
ataggggtca  gtgttacaac  caattaacca  attctgaaca  ttatcgcgag  cccatttata   960
cctgaatatg  gctcataaca  ccccttgttt  gcctggcggc  agtagcgcgg  tggtcccacc  1020
tgaccccatg  ccgaactcag  aagtgaaacg  ccgtagcgcc  gatggtagtg  tggggactcc  1080
ccatgcgaga  gtagggaact  gccaggcatc  aaataaaacg  aaaggctcag  tcgaaagact  1140
gggccttccg  cccgggctaa  ttaggggtg   tcgcccttat  tcgactctat  agtgaagttc  1200
ctattctcta  gaaagtatag  gaacttctga  agtggggtcg  acttaattaa  ggctgcgcgc  1260
tcgctcgctc  actgaggccg  cccgggcaaa  gcccgggcgt  cgggcgacct  ttggtcgccc  1320
ggcctcagtg  agcgagcgag  cgcgcagaga  gggagtggcc  aactccatca  ctaggggttc  1380
cttgtagtta  atgattaacc  cgccatgcta  cttatctacg  tagcaagcta  gctagttatt  1440
aatagtaatc  aattacgggg  tcattagttc  atagcccata  tatggagttc  cgcgttacat  1500
aacttacggt  aaatgcccg   cctggctgac  cgcccaacga  ccccgccca   ttgacgtcaa  1560
taatgacgta  tgttcccata  gtaacgccaa  tagggacttt  ccattgacgt  caatgggtgg  1620
agtatttacg  gtaaactgcc  cacttggcag  tacatcaagt  gtatcatatg  ccaagtacgc  1680
cccctattga  cgtcaatgac  ggtaaatggc  ccgcctggca  ttatgcccag  tacatgacct  1740
tatgggactt  tcctacttgg  cagtacatct  acgtattagt  catcgctatt  accatggtga  1800
tgcggttttg  gcagtacatc  aatgggcgtg  gatagcggtt  tgactcacgg  ggatttccaa  1860
gtctccaccc  cattgacgtc  aatgggagtt  tgttttggca  ccaaaatcaa  cgggactttc  1920
caaaatgtcg  taacaactcc  gccccattga  cgcaaatggg  cggtaggcgt  gtacggtggg  1980
aggtctatat  aagcagagct  ggtttagtga  accgtcagat  cctgcagaag  ttggtcgtga  2040
ggcactgggc  aggtaagtat  caaggttaca  agacaggttt  aaggagacca  atagaaactg  2100
ggcttgtcga  gacagagaag  actcttgcgt  ttctgatagg  cacctattgg  tcttactgac  2160
atccactttg  cctttctctc  cacaggtgtc  cagccaagat  catgggcggc  cgccatggtg  2220
agcaagggcg  aggagctgtt  caccggggtg  gtgcccatcc  tggtcgagct  ggacggcgac  2280
gtaaacggcc  acaagttcag  cgtgtccggc  gagggcgagg  gcgatgccac  ctacggcaag  2340
ctgaccctga  agttcatctg  caccaccggc  aagctgcccg  tgccctggcc  cacccctgtg  2400
accaccctga  cctacggcgt  gcagtgcttc  agccgctacc  ccgaccacat  gaagcagcac  2460
```

-continued

```
gacttcttca agtccgccat gcccgaaggc tacgtccagg agcgcaccat cttcttcaag    2520
gacgacggca actacaagac ccgcgccgag gtgaagttcg agggcgacac cctggtgaac    2580
cgcatcgagc tgaagggcat cgacttcaag gaggacggca acatcctggg gcacaagctg    2640
gagtacaact acaacagcca caacgtctat atcatggccg acaagcagaa gaacggcatc    2700
aaggtgaact tcaagatccg ccacaacatc gaggacggca gcgtgcagct cgccgaccac    2760
taccagcaga cacccccat cggcgacggc cccgtgctgc tgcccgacaa ccactacctg     2820
agcacccggt ccgccctgag caaagacccc aacgagaagc gcgatcacat ggtcctgctg    2880
gagttcgtga ccgccgccgg gatcactctc ggcatggacg agctgtacaa gtaataagct    2940
tggatccaag agatctgcct cgactgtgcc ttctagttgc cagccatctg ttgtttgccc    3000
ctcccccgtg ccttccttga ccctggaagg tgccactccc actgtccttt cctaataaaa    3060
tgaggaaatt gcatcgcatt gtctgagtag gtgtcattct attctggggg gtggggtggg    3120
gcaggacagc aagggggagg attgggaaga caatagcagg catgctgggg actcgagttc    3180
tacgtagata agtagcatgg cgggttaatc attaactaca aggaacccct agtgatggag    3240
ttggccactc cctctctgcg cgctcgctcg ctcactgagg ccgggcgacc aaaggtcgcc    3300
cgacgcccgg gctttgcccg gcggcctca gtgagcgagc gagcgcgcag ccttaattaa    3360
cctaaggaaa atgaagtgaa gttcctatac tttctagaga ataggaactt ctatagtgag    3420
tcgaataagg gcgacacaaa atttattcta aatgcataat aaatactgat aacatcttat    3480
agtttgtatt atattttgta ttatcgttga catgtataat tttgatatca aaaactgatt    3540 ttcccttat tattttcgag atttattttc ttaattctct ttaacaaact agaaatattg    3600
tatatacaaa aaatcataaa taatagatga atagtttaat tataggtgtt catcaatcga    3660
aaaagcaacg tatcttattt aaagtgcgtt gcttttttct catttataag gttaaataat    3720
tctcatatat caagcaaagt gacaggcgcc cttaaatatt ctgacaaatg ctctttccct    3780
aaactccccc cataaaaaaa cccgccgaag cgggtttta cgttatttgc ggattaacga    3840
ttactcgtta tcagaaccgc ccaggggcc cgagcttaag actggccgtc gttttacaac    3900
acagaaagag tttgtagaaa cgcaaaaagg ccatccgtca ggggccttct gcttagtttg    3960
atgcctggca gttccctact ctcgccttcc gcttcctcgc tcactgactc gctgcgctcg    4020
gtcgttcggc tgcggcgagc ggtatcagct cactcaaagg cggtaatacg gttatccaca    4080
gaatcagggg ataacgcagg aaagaacatg tgagcaaaag gccagcaaaa ggccaggaac    4140
cgtaaaaagg ccgcgttgct ggcgtttttc cataggctcc gccccctga cgagcatcac    4200 aaaaatcgac gctcaagtca gaggtggcga acccgacag gactataaag ataccaggcg    4260 tttccctg gaagctccct cgtgcgctct cctgttccga cctgccgct taccggatac     4320 ctgtccgcct ttctcccttc gggaagcgtg gcgctttctc atagctcacg ctgtaggtat    4380
ctcagttcgg tgtaggtcgt tcgctccaag ctgggctgtg tgcacgaacc cccgttcag    4440 cccgaccgct gcgccttatc cggtaactat cgtcttgagt ccaacccggt aagacacgac    4500
ttatcgccac tggcagcagc cactggtaac aggattagca gagcgaggta tgtaggcggt    4560
gctacagagt tcttgaagtg gtgggctaac tacggctaca ctagaagaac agtatttggt    4620
atctgcgctc tgctgaagcc agttaccttc ggaaaaagag ttggtagctc ttgatccggc    4680
aaacaaacca ccgctggtag cggtggtttt tttgtttgca agcagcagat tacgcgcaga    4740 aaaaaggat ctcaagaaga tcctttgatc ttttctacgg ggtctgacgc tcagtggaac    4800
```

```
gacgcgcgcg taactcacgt taagggattt tggtcatgag cttgcgccgt cccgtcaagt    4860
cagcgtaatg ctctgctttt                                                4879

<210> SEQ ID NO 2
<211> LENGTH: 5060
<212> TYPE: DNA
<213> ORGANISM: Artificial Sequence
<220> FEATURE:
<223> OTHER INFORMATION: proviral plasmid p617 from adeno-associated
      virus

<400> SEQUENCE: 2
tagaaaaact catcgagcat caaatgaaac tgcaatttat tcatatcagg attatcaata      60 ccatatttt gaaaaagccg tttctgtaat gaaggagaaa actcaccgag gcagttccat     120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtgt cgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gctagttatt   1440
aatagtaatc aattacgggg tcattagttc atagcccata tatggagttc cgcgttacat   1500
aacttacggt aaatggcccg cctggctgac cgcccaacga cccccgccca ttgacgtcaa   1560
taatgacgta tgttcccata gtaacgccaa tagggacttt ccattgacgt caatgggtgg   1620
agtatttacg gtaaactgcc cacttggcag tacatcaagt gtatcatatg ccaagtacgc   1680
cccctattga cgtcaatgac ggtaaatggc ccgcctggca ttatgcccag tacatgacct   1740
tatgggactt tcctacttgg cagtacatct acgtattagt catcgctatt aacatggtcg   1800
aggtgagccc cacgttctgc ttcactctcc ccatctcccc ccctccccca ccccaatttt   1860
tgtatttatt tattttttaa ttattttgtg cagcgatggg ggcggggggg ggggggggc    1920
```

```
gcgcgccagg cggggcgggg cggggcgagg ggcggggcgg ggcgaggcgg agaggtgcgg    1980
cggcagccaa tcagagcggc gcgctccgaa agtttccttt tatggcgagg cggcggcggc    2040
ggcggcccta taaaagcga agcgcgcggc gggcggggag tcgctgcgac gctgccttcg    2100
ccccgtgccc cgctccgccg ccgctcgcg ccgcccgccc cggctctgac tgaccgcgtt    2160
actcccacag gtgagcgggc gggacggccc ttctcctccg ggctgtaatt agcgcttggt    2220
ttaatgacgg cttgtttctt ttctgtggct gcgtgaaagc cttgagggc tccgggaggg    2280
cccttttgtgc ggggggagcg gctcgggggg tgcgtgcgtg tgtgtgtgcg tggggagcgc    2340
cgcgtgcggc tccgcgctgc ccggcggctg tgagcgctgc gggcgcggcg cggggctttg    2400
tgcgctccgc agtgtgcgcg aggggagcgc ggccggggc ggtgcccgc ggtgcggggg      2460
gggctgcgag gggaacaaag gctgcgtgcg gggtgtgtgc gtgggggggt gagcagggg     2520
tgtgggcgcg tcggtcgggc tgcaacccc cctgcacccc cctccccgag ttgctgagca    2580
cggcccggct tcgggtgcgg ggctccgtac ggggcgtggc gcggggctcg ccgtgccggg    2640
cggggggtgg cggcaggtgg gggtgccggg cggggcgggg ccgcctcggg ccggagggg    2700
ctcggggag gggcgcggcg gccccggag cgccggcggc tgtcgaggcg cggcgagccg     2760
cagccattgc cttttatggt aatcgtgcga gagggcgcag ggacttcctt tgtcccaaat    2820
ctgtgcggag ccgaaatctg ggaggcgccg ccgcaccccc tctagcgggc gcggggcgaa    2880
gcggtgcggc gccggcagga aggaaatggg cggggagggc cttcgtgcgt cgccgcgccg    2940
ccgtccccttt ctccctctcc agcctcgggg ctgtccgcgg ggggacggct gccttcgggg    3000
gggacgggc agggcggggt tcggcttctg gcgtgtgacc ggcggctcta gacaattgta    3060
ctaaccttct tctcttttcct ctcctgacag gttggtgtac actagcggcc gcatagtact    3120
gcggatcctg cagatctgcc tcgactgtgc cttctagttg ccagccatct gttgtttgcc    3180
cctccccgt gccttccttg accctggaag gtgccactcc cactgtcctt tcctaataaa    3240
atgaggaaat tgcatcgcat tgtcgagta ggtgtcattc tattctgggg ggtggggtgg    3300
ggcaggacag caaggggag gattgggaag acaatagcag gcatgctggg gactcgagtt    3360
ctacgtagat aagtagcatg gcgggttaat cattaactac aaggaaccc tagtgatgga    3420
gttggccact ccctctctgc gcgctcgctc gctcactgag gccgggcgac caaaggtcgc    3480
ccgacgcccg ggctttgccc gggcggcctc agtgagcgag cgagcgcgca gccttaatta    3540
acctaaggaa aatgaagtga agttcctata ctttctagag aataggaact tctatagtga    3600
gtcgaataag ggcgacacaa aatttattct aaatgcataa taaatactga taacatctta    3660
tagtttgtat tatattttgt attatcgttg acatgtataa ttttgatatc aaaaactgat    3720
tttcccttta ttattttcga gatttatttt cttaattctc tttaacaaac tagaaatatt    3780
gtatatacaa aaaatcataa ataatagatg aatagtttaa ttataggtgt tcatcaatcg    3840
aaaaagcaac gtatcttatt taaagtgcgt tgcttttttc tcatttataa ggttaaataa    3900
ttctcatata tcaagcaaag tgacaggcgc ccttaaatat tctgacaaat gctctttccc    3960
taaactcccc ccataaaaaa acccgccgaa gcgggttttt acgttatttg cggattaacg    4020
attactcgtt atcagaaccg cccagggggc ccgagcttaa gactggccgt cgttttacaa    4080
cacagaaaga gtttgtagaa acgcaaaaag gccatccgtc aggggccttc tgcttagttt    4140
gatgcctggc agttccctac tctcgccttc gcttcctcg ctcactgact cgctgcgctc    4200
ggtcgttcgc tgcggcgag cggtatcagc tcactcaaag gcggtaatac ggttatccac    4260
agaatcaggg gataacgcag gaaagaacat gtgagcaaaa ggccagcaaa aggccaggaa    4320
```

```
ccgtaaaaag gccgcgttgc tggcgttttt ccataggctc cgcccccctg acgagcatca    4380
caaaaatcga cgctcaagtc agaggtggcg aaacccgaca ggactataaa gataccaggc    4440
gtttccccct ggaagctccc tcgtgcgctc tcctgttccg accctgccgc ttaccggata    4500
cctgtccgcc tttctccctt cgggaagcgt ggcgctttct catagctcac gctgtaggta    4560
tctcagttcg gtgtaggtcg ttcgctccaa gctgggctgt gtgcacgaac cccccgttca    4620
gcccgaccgc tgcgccttat ccggtaacta tcgtcttgag tccaacccgg taagacacga    4680
cttatcgcca ctggcagcag ccactggtaa caggattagc agagcgaggt atgtaggcgg    4740
tgctacagag ttcttgaagt ggtgggctaa ctacggctac actagaagaa cagtatttgg    4800
tatctgcgct ctgctgaagc cagttacctt cggaaaaaga gttggtagct cttgatccgg    4860
caaacaaacc accgctggta gcggtggttt ttttgtttgc aagcagcaga ttacgcgcag    4920
aaaaaaagga tctcaagaag atcctttgat cttttctacg gggtctgacg ctcagtggaa    4980
cgacgcgcgc gtaactcacg ttaagggatt ttggtcatga gcttgcgccg tcccgtcaag    5040
tcagcgtaat gctctgcttt                                                 5060

<210> SEQ ID NO 3
<211> LENGTH: 10131
<212> TYPE: DNA
<213> ORGANISM: Artificial Sequence
<220> FEATURE:
<223> OTHER INFORMATION: proviral plasmid p618 from adeno-associated
      virus

<400> SEQUENCE: 3
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact     240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca ccccttgttt gcctggcggc agtagcgcgg tggtcccacc    1020
tgaccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttaggggtg tcgcccttat tcgactctat agtgaagttc    1200
ctattctcta gaaagtatag gaacttctga agtggggtcg acttaattaa ggctgcgcgc    1260
```

```
tcgctcgctc actgaggccg cccgggcaaa gcccgggcgt cgggcgacct ttggtcgccc      1320
ggcctcagtg agcgagcgag cgcgcagaga gggagtggcc aactccatca ctaggggttc      1380
cttgtagtta atgattaacc cgccatgcta cttatctacg tagcaagcta gctagttatt      1440
aatagtaatc aattacgggg tcattagttc atagcccata tatggagttc cgcgttacat      1500
aacttacggt aaatggcccg cctggctgac cgcccaacga ccccgccca ttgacgtcaa       1560 taatgacgta tgttcccata gtaacgccaa tagggacttt ccattgacgt caatgggtgg      1620
agtatttacg gtaaactgcc cacttggcag tacatcaagt gtatcatatg ccaagtacgc      1680
cccctattga cgtcaatgac ggtaaatggc ccgcctggca ttatgcccag tacatgacct      1740
tatgggactt tcctacttgg cagtacatct acgtattagt catcgctatt aacatggtcg      1800
aggtgagccc cacgttctgc ttcactctcc ccatctcccc cccctcccca ccccaatt       1860 tgtatttatt tattttttaa ttattttgtg cagcgatggg ggcggggggg ggggggggc      1920 gcgcgccagg cggggcgggg cggggcgagg ggcggggcgg ggcgaggcgg agaggtgcgg     1980
cggcagccaa tcagagcggc gcgctccgaa agtttccttt tatggcgagg cggcggcggc     2040
ggcggcccta taaaaagcga agcgcgcggc gggcggggag tcgctgcgac gctgccttcg     2100
ccccgtgccc cgctccgccg ccgcctcgcg ccgcccgccc cggctctgac tgaccgcgtt     2160
actcccacag gtgagcgggc gggacggccc ttctcctccg ggctgtaatt agcgcttggt     2220
ttaatgacgg cttgtttctt ttctgtggct gcgtgaaagc cttgagggc tccgggaggg      2280 cccttttgtgc gggggagcg gctcgggggg tgcgtgcgtg tgtgtgtgcg tggggagcgc     2340
cgcgtgcggc tccgcgctgc ccggcggctg tgagcgctgc gggcgcggcg cggggctttg    2400
tgcgctccgc agtgtgcgcg aggggagcgc ggccggggc ggtgcccgc ggtgcgggg       2460 gggctgcgag gggaacaaag gctgcgtgcg gggtgtgtgc gtgggggggt gagcagggg     2520 tgtgggcgcg tcggtcgggc tgcaacccc cctgcacccc cctccccgag ttgctgagca     2580
cggcccggct tcgggtgcgg ggctccgtac ggggcgtggc gcgggctcg ccgtgccggg     2640 cggggggtgg cggcaggtgg gggtgccggg cgggcgggg ccgcctcggg ccggggaggg    2700 ctcggggag gggcgcggcg gcccccgag cgccggcggc tgtcgaggcg cggcgagccg      2760
cagccattgc ctttatggt aatcgtgcga gagggcgcag ggacttcctt tgtcccaaat      2820
ctgtgcggag ccgaaatctg ggaggcgccg ccgcacccc tctagcgggc gcggggcgaa      2880
gcggtgcggc ccggcagga aggaaatggg cggggaggg cttcgtgcgt cgccgcgccg     2940
ccgtcccctt ctccctctcc agcctcgggg ctgtccgcgg ggggacggct gccttcgggg     3000
gggacggggc agggcgggt tcggcttctg gcgtgtgacc ggcggctcta gacaattgta     3060
ctaaccttct tctctttcct ctcctgacag gttggtgtac actagcggcc gcatagtact     3120
gcggatcctg cagatctgcc tcgactgtgc cttctagttg ccagccatct gttgtttgcc     3180
cctcccccgt gccttccttg accctggaag gtgccactcc cactgtcctt tcctaataaa    3240
atgaggaaat tgcatcgcat tgtctgagta ggtgtcattc tattctgggg ggtggggtgg     3300
ggcaggacag caaggggag gattgggaag acaatagcag gcatgctggg gactcgagtt     3360
ctacgtagat aagtagcatg gcgggttaat cattaactac aaggaacccc tagtgatgga     3420
gttggccact ccctctctgc gcgctcgctc gctcactgag gccgggcgac caaaggtcgc     3480
ccgacgcccg ggctttgccc gggcggcctc agtgagcgag cgagcgcgca gccttaatta     3540
acctaaggaa aatgaagtga agttcctata ctttctagag aataggaact tctatagtga     3600
```

```
gtcgaataag ggcgacacaa aatttattct aaatgcataa taaatactga taacatctta    3660
tagtttgtat tatattttgt attatcgttg acatgtataa ttttgatatc aaaaactgat    3720
tttcccttta ttattttcga gatttatttt cttaattctc tttaacaaac tagaaatatt    3780
gtatatacaa aaaatcataa ataatagatg aatagtttaa ttataggtgt tcatcaatcg    3840
aaaaagcaac gtatcttatt taaagtgcgt tgctttttc tcatttataa ggttaaataa     3900
ttctcatata tcaagcaaag tgacaggcgc ccttaaatat tctgacaaat gctctttccc    3960
taaactcccc ccataaaaaa acccgccgaa gcgggttttt acgttatttg cggattaacg    4020
attactcgtt atcagaaccg cccaggggc ccgagcttaa cctttttatt tgggggagag     4080
ggaagtcatg aaaaaactaa cctttgaaat tcgatctcca gcacatcagc aaaacgctat    4140
tcacgcagta cagcaaatcc ttccagaccc aaccaaacca atcgtagtaa ccattcagga    4200
acgcaaccgc agcttagacc aaaacaggaa gctatgggcc tgcttaggtg acgtctctcg    4260
tcaggttgaa tggcatggtc gctggctgga tgcagaaagc tggaagtgtg tgtttaccgc    4320
agcattaaag cagcaggatg ttgttcctaa ccttgccggg aatggctttg tggtaatagg    4380
ccagtcaacc agcaggatgc gtgtaggcga atttgcggag ctattagagc ttatacaggc    4440
attcggtaca gagcgtggcg ttaagtggtc agacgaagcg agactggctc tggagtggaa    4500
agcgagatgg ggagacaggg ctgcatgata aatgtcgtta gtttctccgg tggcaggacg    4560
tcagcatatt tgctctggct aatggagcaa aagcgacggg caggtaaaga cgtgcattac    4620
gttttcatgg atacaggttg tgaacatcca atgacatatc ggtttgtcag ggaagttgtg    4680
aagttctggg atataccgct caccgtattg caggttgata tcaacccgga gcttggacag    4740
ccaaatggtt atacggtatg ggaaccaaag gatattcaga cgcgaatgcc tgttctgaag    4800
ccatttatcg atatggtaaa gaaatatggc actccatacg tcggcggcgc gttctgcact    4860
gacagattaa aactcgttcc cttcaccaaa tactgtgatg accatttcgg gcgagggaat    4920
tacaccacgt ggattggcat cagagctgat gaaccgaagc ggctaaagcc aaagcctgga    4980
atcagatatc ttgctgaact gtcagacttt gagaaggaag atatcctcgc atggtggaag    5040
caacaaccat tcgatttgca ataccggaaa catctcggta actgcatatt ctgcattaaa    5100
aaatcaacgc aaaaaatcgg acttgcctgc aaagatgagg agggattgca gcgtgttttt    5160
aatgaggtca tcacgggatc ccatgtgcgt gacggacatc gggaaacgcc aaaggagatt    5220
atgtaccgag gaagaatgtc gctggacggt atcgcgaaaa tgtattcaga aaatgattat    5280
caagccctgt atcaggacat ggtacgagct aaaagattcg ataccggctc ttgttctgag    5340
tcatgcgaaa tatttggagg gcagcttgat ttcgacttcg ggagggaagc tgcatgatgc    5400
gatgttatcg gtgcggtgaa tgcaaagaag ataccgcctt ccgaccaaat caaccttact    5460
ggaatcgatg gtgtctccgg tgtgaaagaa caccaacagg ggtgttacca ctaccgcagg    5520
aaaaggagga cgtgtggcga gacagcgacg aagtatcacc gacataatct gcgaaaactg    5580
caaatacctt ccaacgaaac gcaccagaaa taaacccaag ccaatcccaa agaatctga    5640
cgtaaaaacc ttcaactaca cggctcacct gtgggatatc cggtggctaa gacgtcgtgc    5700
gaggaaaaca aggtgattga ccaaaatcga agttacgaac aagaaagcgt cgagcgagct    5760
ttaacgtgcg ctaactgcgg tcagaagctg catgtgctgg aagttcacgt gtgtgagcac    5820
tgctgcgcag aactgatgag cgatccgaat agctcgatgc acgaggaaga agatgatggc    5880
taaaccagcg cgaagacgat gtaaaaacga tgaatgccgg gaatggtttc accctgcatt    5940
cgctaatcag tggtggtgct ctccagagtg tggaaccaag atagcactcg aacgacgaag    6000
```

```
taaagaacgc gaaaaagcgg aaaaagcagc agagaagaaa cgacgacgag aggagcagaa      6060
acagaaagat aaacttaaga ttcgaaaact cgccttaaag ccccgcagtt actggattaa      6120
acaagcccaa caagccgtaa acgccttcat cagagaaaga gaccgcgact taccatgtat      6180
ctcgtgcgga acgctcacgt ctgctcagtg ggatgccgga cattaccgga caactgctgc      6240
ggcacctcaa ctccgattta atgaacgcaa tattcacaag caatgcgtgg tgtgcaacca      6300
gcacaaaagc ggaaatctcg ttccgtatcg cgtcgaactg attagccgca tcgggcagga      6360
agcagtagac gaaatcgaat caaaccataa ccgccatcgc tggactatcg aagagtgcaa      6420
ggcgatcaag gcagagtacc aacagaaact caaagacctg cgaaatagca gaagtgaggc      6480
cgcatgacgt tctcagtaaa aaccattcca gacatgctcg ttgaagcata cggaaatcag      6540
acagaagtag cacgcagact gaaatgtagt cgcggtacgg tcagaaaata cgttgatgat      6600
aaagacggga aaatgcacgc catcgtcaac gacgttctca tggttcatcg cggatggagt      6660
gaaagagatg cgctattacg aaaaaattga tggcagcaaa taccgaaata tttgggtagt      6720
tggcgatctg cacggatgct acacgaacct gatgaacaaa ctggatacga ttggattcga      6780
caacaaaaaa gacctgctta tctcggtggg cgatttggtt gatcgtggtg cagagaacgt      6840
tgaatgcctg gaattaatca cattccctg gttcagagct gtacgtggaa accatgagca      6900
aatgatgatt gatggcttat cagagcgtgg aaacgttaat cactggctgc ttaatggcgg      6960
tggctggttc tttaatctcg attacgacaa agaaattctg gctaaagctc ttgcccataa      7020
agcagatgaa cttccgttaa tcatcgaact ggtgagcaaa gataaaaaat atgttatctg      7080
ccacgccgat tatcccttg acgaatacga gtttggaaag ccagttgatc atcagcaggt      7140
aatctggaac cgcgaacgaa tcagcaactc acaaaacggg atcgtgaaag aaatcaaagg      7200
cgcggacacg ttcatctttg gtcatacgcc agcagtgaaa ccactcaagt ttgccaacca      7260
aatgtatatc gataccggcg cagtgttctg cggaaaccta acattgattc aggtacaggg      7320
agaaggcgca tgagactcga agcgtagct aaatttcatt cgccaaaaag cccgatgatg      7380
agcgactcac cacgggccac ggcttctgac tctctttccg gtactgatgt gatggctgct      7440
atggggatgg cgcaatcaca agccggattc ggtatggctg cattctgcgg taagcacgaa      7500
ctcagccaga acgacaaaca aaaggctatc aactatctga tgcaatttgc acacaaggta      7560
tcggggaaat accgtggtgt ggcaaagctt gaaggaaata ctaaggcaaa ggtactgcaa      7620
gtgctcgcaa cattcgctta tgcggattat tgccgtagtg ccgcgacgcc ggggcaaga      7680 tgcagagatt gccatggtac aggccgtgcg gttgatattg ccaaaacaga gctgtggggg      7740
agagttgtcg agaaagagtg cggaagatgc aaaggcgtcg gctattcaag gatgccagca      7800
agcgcagcat atcgcgctgt gacgatgcta atcccaaacc ttacccaacc cacctggtca      7860
cgcactgtta agccgctgta tgacgctctg gtggtgcaat gccacaaaga agagtcaatc      7920
gcagacaaca ttttgaatgc ggtcacacgt tagcagcatg attgccacgg atggcaacat      7980
attaacggca tgatattgac ttattgaata aaatttgggta aatttgactc aacgatgggt      8040
taattcgctc gttgtggtag tgagatgaaa agaggcggcg cttactaccg attccgccta      8100
gttggtcact tcgacgtatc gtctggaact ccaaccatcg caggcagaga ggtctgcaaa      8160
atgcaatccc gaaacagttc gcaggtaata gttagagcct gcataacggt ttcgggattt      8220
tttatatctg cacaacaggt aagagcattg agtcgataat cgtgaagagt cggcgagcct      8280
ggttagccag tgctctttcc gttgtgctga attaagcgaa taccggaagc agaaccggat      8340
```

-continued

```
caccaaatgc gtacaggcgt catcgccgcc cagcaacagc acaacccaaa ctgagccgta      8400
gccactgtct gtcctgaatt cattagtaat agttacgctg cggccttttta cacatgacct     8460 tcgtgaaagc gggtggcagg aggtcgcgct aacaacctcc tgccgttttg cccgtgcata      8520
tcggtcacga acaaatctga ttactaaaca cagtagcctg gatttgttct atcagtaatc      8580
gaccttattc ctaattaaat agagcaaatc cccttattgg gggtaagaca tgaagatgcc      8640
agaaaaacat gacctgttgg ccgccattct cgcggcaaag gaacaaggca tcggggcaat      8700
ccttgcgttt gcaatggcgt accttcgcgg cagatataat ggcggtgcgt ttacaaaaac      8760
agtaatcgac gcaacgatgt gcgccattat cgcctggttc attcgtgacc ttctcgactt      8820
cgccggacta agtagcaatc tcgcttatat aacgagcgtg tttatcggct acatcggtac      8880
tgactcgatt ggttcgctta tcaaacgctt cgctgctaaa aaagccggag tagaagatgg      8940
tagaaatcaa taatcaacgt aaggcgttcc tcgatatgct ggcgtggtcg gagggaactg      9000 ataacgacg tcagaaaacc agaaatcatg gttatgacgt cattgtaggc ggagagctat       9060
ttactgatta ctccgatcac cctcgcaaac ttgtcacgct aaacccaaaa ctcaaatcaa      9120
caggcgctta agactggccg tcgttttaca acacagaaag agtttgtaga aacgcaaaaa      9180
ggccatccgt caggggcctt ctgcttagtt tgatgcctgg cagttcccta ctctcgcctt      9240
ccgcttcctc gctcactgac tcgctgcgct cggtcgttcg gctgcggcga gcggtatcag      9300
ctcactcaaa ggcggtaata cggttatcca cagaatcagg gataacgca ggaaagaaca       9360 tgtgagcaaa aggccagcaa aaggccagga accgtaaaaa ggccgcgttg ctggcgtttt      9420
tccataggct ccgcccccct gacgagcatc acaaaaatcg acgctcaagt cagaggtggc      9480
gaaacccgac aggactataa agataccagg cgtttccccc tggaagctcc ctcgtgcgct      9540
ctcctgttcc gaccctgccg cttaccggat acctgtccgc ctttctccct tcgggaagcg      9600
tggcgctttc tcatagctca cgctgtaggt atctcagttc ggtgtaggtc gttcgctcca      9660
agctgggctg tgtgcacgaa ccccccgttc agcccgaccg ctgcgcctta tccggtaact      9720
atcgtcttga gtccaacccg gtaagacacg acttatcgcc actggcagca gccactggta      9780
acaggattag cagagcgagg tatgtaggcg gtgctacaga gttcttgaag tggtgggcta      9840
actacggcta cactagaaga acagtatttg gtatctgcgc tctgctgaag ccagttacct      9900
tcggaaaaag agttggtagc tcttgatccg gcaaacaaac caccgctggt agcggtggtt      9960 ttttgtttg caagcagcag attacgcgca gaaaaaaagg atctcaagaa gatcctttga       10020
tcttttctac ggggtctgac gctcagtgga acgacgcgcg cgtaactcac gttaagggat      10080
tttggtcatg agcttgcgcc gtcccgtcaa gtcagcgtaa tgctctgctt t              10131
```

<210> SEQ ID NO 4
<211> LENGTH: 456
<212> TYPE: DNA
<213> ORGANISM: Homo sapiens

<400> SEQUENCE: 4

```
gagaggagcc agtcagcaga ccggggacca cacgccgcgc tgtccccagc acccaaccca       60
ggttaccatg gcctccctgt tctctggccg catcctgatc cgcaacaata gcgaccagga      120
cgagctggat acggaggctg aggtcagtcg caggctggag aaccggctgg tgctgctgtt      180
ctttggtgct ggggcttgtc cacagtgcca ggccttcgtg cccatcctca aggacttctt      240
cgtgcggctc acagatgagt tctatgtact gcgggcggct cagctggccc tggtgtacgt      300
gtcccaggac tccacggagg agcagcagga cctgttcctc aaggacatgc caaagaaatg      360
```

```
gcttttcctg ccctttgagg atgatctgag gaggtgagga ggggcaggga gggcttcctg      420
gaggaggggg catgttcgct gaaagtgaag catcca                                456

<210> SEQ ID NO 5
<211> LENGTH: 327
<212> TYPE: DNA
<213> ORGANISM: Homo sapiens

<400> SEQUENCE: 5
atggcctccc tgttctctgg ccgcatcctg atccgcaaca atagcgacca ggacgagctg       60
gatacggagg ctgaggtcag tcgcaggctg gagaaccggc tggtgctgct gttctttggt      120 gctgggctt gtccacagtg ccaggccttc gtgcccatcc tcaaggactt cttcgtgcgg       180
ctcacagatg agttctatgt actgcgggcg gctcagctgg ccctggtgta cgtgtcccag      240
gactccacgg aggagcagca ggacctgttc ctcaaggaca tgccaaagaa atggcttttc      300
ctgccctttg aggatgatct gaggagg                                          327

<210> SEQ ID NO 6
<211> LENGTH: 49
<212> TYPE: DNA
<213> ORGANISM: Unknown
<220> FEATURE:
<223> OTHER INFORMATION: cytomegalovirus

<400> SEQUENCE: 6
tagtaatcaa ttacggggtc attagttcat agcccatata tggagttcc                   49
```